(12) United States Patent
Pouchoulin

(10) Patent No.: US 12,318,529 B2
(45) Date of Patent: Jun. 3, 2025

(54) APPARATUS FOR EXTRACORPOREAL TREATMENT OF BLOOD

(71) Applicant: GAMBRO LUNDIA AB, Lund (SE)

(72) Inventor: Dominique Pouchoulin, Tramoyes (FR)

(73) Assignee: GAMBRO LUNDIA AB, Lund (SE)

( * ) Notice: Subject to any disclaimer, the term of this patent is extended or adjusted under 35 U.S.C. 154(b) by 92 days.

(21) Appl. No.: 16/936,659

(22) Filed: Jul. 23, 2020

(65) Prior Publication Data
US 2020/0345922 A1    Nov. 5, 2020

Related U.S. Application Data

(63) Continuation of application No. 13/876,357, filed as application No. PCT/IB2011/002098 on Sep. 8, 2011, now Pat. No. 10,737,011.

(30) Foreign Application Priority Data

Sep. 27, 2010    (EP) .................................... 10010805

(51) Int. Cl.
*A61M 1/36*    (2006.01)
*A61M 1/16*    (2006.01)
*A61M 1/34*    (2006.01)

(52) U.S. Cl.
CPC ............ *A61M 1/3663* (2013.01); *A61M 1/16* (2013.01); *A61M 1/1601* (2014.02); *A61M 1/1643* (2014.02); *A61M 1/3434* (2014.02); *A61M 1/3437* (2014.02); *A61M 1/3441* (2013.01); *A61M 1/3451* (2014.02); *A61M 2205/3393* (2013.01); *A61M 2205/505* (2013.01)

(58) Field of Classification Search
None
See application file for complete search history.

(56) References Cited

U.S. PATENT DOCUMENTS

| | | | | |
|---|---|---|---|---|
| 5,656,153 A | * | 8/1997 | Kameno | A61M 1/1601 210/138 |
| 2005/0085760 A1 | * | 4/2005 | Ware | A61M 1/3441 604/4.01 |

* cited by examiner

*Primary Examiner* — Jonathan M Peo
(74) *Attorney, Agent, or Firm* — K&L Gates LLP

(57) ABSTRACT

An apparatus for extracorporeal treatment of blood comprising a filtration unit, a blood withdrawal line, a blood return line, an effluent fluid line, a pre and/or post-dilution fluid line connected to the blood withdrawal line, and a dialysis fluid line. Pumps act on the fluid lines for regulating the flow of fluid. A control unit is configured to set initial values to one or more fluid flow rates through the above lines and to periodically execute a flow rate update procedure in order to deliver a set dose ($D_{set}$) in a reference time interval.

13 Claims, 5 Drawing Sheets

APPARATUS FOR EXTRACORPOREAL TREATMENT OF BLOOD

PRIORITY CLAIM

The present application is a continuation of U.S. application Ser. No. 13/876,357, filed Jun. 10, 2013, now U.S. Pat. No. 10,737,011, which is a National Phase of International Application No. PCT/IB2011/002098, filed Sep. 8, 2011, which claims priority to EP Application No. 10010805.9, filed Sep. 27, 2010. The entire contents of each application listed above is herein incorporated by reference and relied upon.

DESCRIPTION

The present invention relates to an apparatus for extracorporeal treatment of blood.

Extracorporeal blood treatment involves removing blood from a patient, treating the blood externally to the patient, and returning the treated blood to the patient. Extracorporeal blood treatment is typically used to extract undesirable matter or molecules from the patient's blood and/or add desirable matter or molecules to the blood. Extracorporeal blood treatment is used with patients unable to effectively remove matter from their blood, such as when a patient has suffered temporary or permanent kidney failure. These patients and other patients may undergo extracorporeal blood treatment to add or remove matter to their blood, to maintain an acid/base balance or to remove excess body fluids, for example.

Extracorporeal blood treatment is typically accomplished by removing the blood from the patient in e.g. a continuous flow, introducing the blood into a primary chamber, also referred to as blood chamber, of a filtration unit (such as a dialyzer or an hemofilter) where the blood is allowed to flow past a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment.

A number of different types of extracorporeal blood treatments may be performed. In an ultrafiltration (UF) treatment, undesirable matter is removed from the blood by convection across the membrane into the secondary chamber. In a hemofiltration (HF) treatment, the blood flows past the semipermeable membrane as in UF and desirable matter is added to the blood, typically by dispensing a fluid into the blood either before and/or after it passes through the filtration unit and before it is returned to the patient. In a hemodialysis (HD) treatment, a secondary fluid containing desirable matter is introduced into the secondary chamber of the filtration unit. Undesirable matter from the blood crosses the semipermeable membrane into the secondary fluid and desirable matter from the secondary fluid may cross the membrane into the blood. In a hemodiafiltration (HDF) treatment, blood and secondary fluid exchange matter as in HD, and, in addition, matter is added to the blood, typically by dispensing a fluid into the treated blood before its return to the patient as in HF.

Specific blood treatment apparatus have been developed for the treatment of acute patients mainly because:

in acute patients, the total treatment time is a priori unknown and, as such, it may not be used as setup parameter as it is not known how long kidney insufficiency will be present; indeed, acute patients often need relatively long treatment sessions, typically lasting several days, before recovering from kidney failure;

intensive care apparatus may rather be designed to request a plurality of flow rate information as setup parameters;

acute patients need a very precisely controlled fluid removal; moreover, infusion of drugs or of fluids in general shall also be very accurately controlled;

acute patients are also very weak; thus, in the course of the treatment of acute patients it has been regarded as relevant to make sure that a continuous and gentle therapy is delivered to the patient during treatment with a very accurate control on the flow rate in each of the lines connected with the bloodlines;

furthermore, apparatus often need to be operated in emergency situations, thus apparatus for acute treatment shall be characterized by very easy to set up procedures.

In this situation, blood treatment apparatus have been developed presenting infusion lines for supplying fluid upstream or downstream the filtration unit, a fresh dialysis liquid line for supplying liquid to the dialysate chamber of the filtration unit, and a waste line receiving spent dialysis fluid and ultrafiltered fluid from filtration unit. In correspondence of each of the above lines, means for generating a flow rate is acting, such as a peristaltic pump which is rotated under the supervision of a control unit. Moreover, fluid containers supply fluid to the infusion lines and to the dialysate line, while a waste container or a waste handling system receives the spent liquid from the waste line. Typically, scales are used to weigh the fluid containers and to provide signals used by the control unit to control the pumps or other actuators on the fluid lines so that the apparatus achieves the fluid removal rate set by the user, and—depending upon the apparatus—any other rates through each line. In more sophisticated solutions, each of the above lines receives fluid from a respective container which, in use, is associated to a respective scale and cooperates with a respective pump. A user interface allows an operator entering the fluid loss rate and the fluid flow rates of each of the substitution lines and dialysate line such that the apparatus is capable of continuously keep under control the amount of fluid infused, the amount of fluid flowing through the dialysate line and the fluid loss rate.

Although the above solution results in a very efficient apparatus able to perform all necessary treatments and to accurately control the flows, the applicant has found ways to further improve known blood treatment apparatuses.

It is an object of the present invention to render available a blood treatment apparatus suitable for intensive care applications which can also be automatically able to deliver prescribed doses, without however compromising the operating philosophy of an intensive care apparatus.

Furthermore, it is an object of the invention an apparatus which is able to take into account the effective portions of the treatment procedure, possibly adapting one or more values of certain set-up parameters to account for machine stops, therapy delivery interruptions, machine downtimes, such as to deliver a prescribed doses during certain time intervals of reference.

A further object of the present invention is an apparatus for the performance of an extracorporeal blood treatment by automatically calculating, performing and monitoring the extracorporeal blood treatment based upon a choice of a treatment and of a prescription by the operator.

Another object is an apparatus capable of controlling all operating parameters in a safe manner.

Another object is to automatically ascertain whether certain prescription targets cannot be achieved and inform the operator accordingly.

Another object is to notify the operator of conditions requiring operator assistance.

SUMMARY

At least one of the above objects is substantially reached by an apparatus according to one or more of the appended claims.

Apparatus and processes for the extracorporeal treatment of blood according to aspects of the invention are here below described.

A first aspect relates to an apparatus for extracorporeal treatment of blood comprising a filtration unit having a primary chamber and a secondary chamber separated by a semi-permeable membrane; a blood withdrawal line connected to an inlet of the primary chamber, and a blood return line connected to an outlet of the primary chamber said blood lines being designed to be connected to a patient cardiovascular system; a blood pump for controlling the flow of blood through the blood lines; an effluent fluid line connected to an outlet of the secondary chamber; at least one fluid line selected in the group comprising: one or more infusion fluid lines connected to one of the blood withdrawal line and the blood return line, and a dialysis fluid line connected to the inlet of the secondary chamber; means for regulating the flow of fluid through said fluid lines, and a control unit configured to:
- set initial values to one or more fluid flow rates selected in the group including a fluid flow rate ($Q_{eff}$) through the effluent line, a fluid flow rate ($Q_{rep}$, $Q_{pbp}$) through the infusion fluid line, a fluid flow rate ($Q_{dial}$) through the dialysis liquid fluid line, and a fluid removal rate ($Q_{pfr}$) from the patient,
- calculate or receive (the dose can either be entered by a user or stored as a set value or calculated based on the set initial values for the mentioned fluid flow rates) at least a prescribed dose ($D_{set}$), said prescribed dose being a target mean value of a flow rate to be delivered through a patient treatment,
- execute a flow rate update procedure comprising calculating an updated set of values for one or more of said fluid flow rates based on said prescribed dose ($D_{set}$), such that said prescribed dose is matched ($D_{set}$) during each one (or during a least some) of a plurality reference time intervals across the patient treatment,
- control said means for regulating the flow of fluid based on said updated set values.

For instance, initial values can be set for the fluid flow rate ($Q_{rep}$, $Q_{pbp}$) through the infusion fluid line, the fluid flow rate ($Q_{dial}$) through the dialysis liquid fluid line (if this line is present and used), and the fluid removal rate ($Q_{pfr}$) from the patient. The effluent fluid flow rate can then be calculated as sum of the above flow rates. Then, based on the set dose, the set flow rates values are updated and the means for regulating controlled with the updated set values. As the patient treatment time may be unknown, the control procedure makes sure that the prescribed dose is achieved during time intervals of reference of a defined duration into which the entire treatment time gets progressively divided.

In a $2^{nd}$ aspect according to the $1^{st}$ aspect, said prescribed dose comprises one flow rate selected in the group including:
- effluent dose flow rate ($D_{eff\_set}$), which is the prescribed mean value of the flow rate through the effluent line,
- convective dose flow rate ($D_{conv\_set}$), which is the prescribed mean value of the sum of the flow rates through any infusion fluid line ($Q_{rep}$, $Q_{pbp}$) and the patient fluid removal rate ($Q_{pfr}$),
- diffusive dose flow rate ($D_{dial\_set}$): which is the prescribed mean value of the flow rate through the dialysis fluid line ($Q_{dial}$),
- urea dose ($D_{urea\_set}$): which is a prescribed mean value for an estimated urea clearance,
- clearance dose ($K_{solute\_set}$): which is a prescribed mean value for an estimated clearance for a given solute.

In a $3^{rd}$ aspect according to any one of $1^{st}$ or $2^{nd}$ aspect, the control unit is configured to regularly, e.g. periodically or according to a predetermined time rule, execute said flow update procedure at check points (Ti) during treatment.

In a $4^{th}$ aspect according to any one of $1^{st}$ or $2^{nd}$ or $3^{rd}$ aspect, the flow update procedure comprises the following steps:
- determining a value of the dose delivered ($D_{del}$) over a time interval ($T_{retro}$) preceding a check point ($T_i$);
- determining a dose need value ($D_{need}$) based at least on the dose delivered value and on the prescribed dose value ($D_{set}$);
- calculating the updated set of values for said fluid flow rates based on said dose need value.

In a $5^{th}$ aspect according to any one of the preceding aspects, the step of determining a dose need value at a check point ($T_i$) comprises computing the dose needed to be delivered over a next time period ($T_{prosp}$) following the check point ($T_i$) in order to reach the prescribed dose over a time interval (which is one of the mentioned reference time intervals) which is the sum of the time interval ($T_{retro}$) preceding check point ($T_i$) and the next time period ($T_{prosp}$).

In a $6^{th}$ aspect according to the $5^{th}$ aspect, the dose need value is calculated according to the formula:

$$D\_need = \frac{D\_set \times T\_prosp + (D\_set - D\_del) \times T\_retro}{T\_prosp}$$

where:
- $D_{del}$ is the dose delivered over a time interval ($T_{retro}$) preceding a check point ($T_i$);
- $D_{need}$ is the dose need value,
- $T_{retro}$ is a time interval preceding check point ($T_i$),
- $T_{prosp}$ is the next time period following the check point ($T_i$),
- $D_{set}$ is the prescribed dose value over a time interval which is the sum of the time interval ($T_{retro}$) preceding check point ($T_i$) and the next time period ($T_{prosp}$).

In a $7^{th}$ aspect according to any one of the preceding aspects, the control unit can additionally be programmed to determine an effective portion ($T_{eff}$) of said next time period. The effective portion of a time period is the portion during which the treatment is actually delivered to the patient, i.e. the period during which the blood pump and the pumps corresponding to the selected treatment actually run and circulate the respective fluids along the respective lines.

In a $8^{th}$ aspect according to the $7^{th}$ aspect the control unit is programmed or configure to calculate a corrected dose value ($D_{computed}$) as follows:

$$D\_computed = D\_need \times \frac{T\_prosp}{T\_eff}$$

In a 9$^{th}$ aspect according to the 8$^{th}$ aspect, the control unit is configured to execute the flow update procedure also taking into account for said effective portion (T$_{eff}$) to be expected over the next time period (T$_{prosp}$) by calculating the updated set of values for said fluid flow rates based on said corrected dose value (D$_{computed}$).

In a 10$^{th}$ aspect according to any one of the preceding aspects the control unit is programmed to allow selection (for instance through a user interface) of one of a plurality of treatment modes, said treatment modes comprising at least two of hemodialysis (HD), hemofiltration with pre-dilution (HF$_{pre}$), hemofiltration with post-dilution (HF$_{post}$), hemofiltration with both pre-dilution and post-dilution (HF$_{pre-post}$), hemodiafiltration with pre-dilution (HDF$_{pre}$), hemodiafiltration with post-dilution (HDF$_{post}$), hemodiafiltration with both pre-dilution and post-dilution (HDF$_{pre-post}$), ultrafiltration (UF), and to control the means for regulating based on the treatment mode selection.

In an 11$^{th}$ aspect according to any one of aspects from 2$^{nd}$ to 10$^{th}$, wherein the control unit is configured to allow selection of one or more dose options (for instance through a user interface), each dose option specifying a respective one of said prescribed doses which a user can select to be the dose placed under control.

In a 12$^{th}$ aspect to claim the 11$^{th}$ aspect the calculation of said updated set of flow rate value or values is also based on said treatment selection and on said dose option selection. In other words depending upon the selected treatment, the control unit decides which are the specific pumps under control (for instance if the treatment is HF, then the dialysis pump is not used at all), and depending upon the dose option and set dose value Dset, the control unit is configured to update at time intervals the set of flow rates accordingly.

In a 13$^{th}$ aspect according to any one of the preceding aspects, the apparatus further comprises a user interface connected to said control unit, said control unit being configured to:
display on the user interface an indicium prompting a user to select whether to enter in a dose control mode,
execute said flow rate update procedure if the user selects to enter in the dose control mode.

In a 14$^{th}$ aspect according to the 13$^{th}$ aspect the control unit is further configured to:
display on the user interface an indicium prompting a user to enter said initial set values of said fluid flow rates,
receive said initial set values,
detect if the user selects said dose control mode, and
if the user selects to enter in the dose control mode, calculate the prescribed dose based on said initial set values.

In a 15$^{th}$ aspect according to the 13$^{th}$ aspect the control unit is further configured to:
detect if the user selects to enter in dose control mode,
if the user selects to enter in the dose control mode, display an indicium prompting a user to enter the prescribed dose, and optionally
calculate said initial values of said flow rates based on said prescribed dose.

In a 16$^{th}$ aspect according to any one of the preceding aspects, said flow rate update procedure comprises:
displaying on a user interface said calculated updated set of values for said flow rates,
prompting user to confirm said updated set of values for said flow rates.

In a 17$^{th}$ aspect according to the 16$^{th}$ aspect the update procedure includes the steps of checking if the user approved the updated set of flow rate values and, only if the user has approved the updated set of values, controlling said means based on said updated set of values for said flow rates. In other words the control unit may be configured to implement the updated values for the flow rates only after approval from the user.

In an 18$^{th}$ aspect according to any one of the preceding aspects, the control unit is further configured to start a treatment controlling said means for regulating based on said initial set of flow rates; and at time periods execute said flow rate update procedure or the control unit is further configured to execute the flow update procedure before treatment start and at time intervals after treatment start.

In a 19$^{th}$ aspect according to any one of the preceding aspects said control unit 10 is further configured to:
start a treatment controlling said means for regulating based on said initial set of flow rates and, subsequent to the occurrence of a triggering event, execute said flow rate update procedure, or
to execute said flow update procedure at least once before treatment start and then after treatment start subsequent to the occurrence of a triggering event,
wherein said triggering event is one selected in the group comprising: expiration of a prefixed time period, change in the value set for the prescribed dose (D$_{set}$), change in blood pump flow rate beyond a prefixed threshold, occurrence of a recirculation of blood beyond a prefixed threshold between the blood return line and the blood withdrawal line.

In a 20$^{th}$ aspect according to any one of the preceding aspects said one or more infusion fluid lines comprise a pre-dilution fluid line connected to the blood withdrawal line and/or a post-dilution fluid line connected to the blood return line; in this case, the means for regulating the flow of fluid through said fluid lines comprises at least an infusion pump for regulating the flow through said pre-dilution fluid line and/or through said post-dilution fluid line.

In a 21$^{st}$ aspect according to the 20$^{th}$ aspect the means for regulating the flow of fluid through said fluid lines comprises a pre-dilution pump for regulating the flow through said pre-dilution fluid line and a post-dilution pump for regulating the flow through said post-dilution fluid line.

In a 22$^{nd}$ aspect according to any one of the preceding aspects the apparatus comprises a dialysis fluid line connected to the inlet of the secondary chamber; in this case the means for regulating the flow of fluid through said fluid lines comprises at least a dialysis fluid pump for regulating the flow through said dialysis fluid line.

In a 23$^{rd}$ aspect according to any one of the preceding aspects said one or more infusion fluid lines comprise a pre-blood pump infusion line connected to the blood withdrawal line in a region of this latter which is positioned, in use, upstream the blood pump; in this case, the means for regulating the flow of fluid through said fluid lines comprises at least a pre-blood infusion pump for regulating the flow through said pre-blood pump infusion fluid.

In a 24$^{th}$ aspect according to any one of aspects from 20$^{th}$ to 23$^{rd}$ the step of calculating the updated set of values comprises calculating an updated infusion pump flow rate and an updated dialysis pump flow rate.

In a 25$^{th}$ aspect according to the 24$^{th}$ aspect said step of calculating the updated infusion pump flow rate and updated dialysis pump flow rate comprises changing the infusion pump flow rate and the dialysis fluid flow rate from their respective initial values by a same percentage.

In a 26$^{th}$ aspect according to any one of the preceding aspects the step of calculating the updated set of values comprises changing value of one of the infusion pump flow rate and the dialysis pump flow rate, without changing the value of the other.

In a 27th aspect according to any one of aspects from 20th to 26th calculating an updated infusion pump flow rate comprises calculating an updated pre-dilution pump flow rate and an updated post-dilution pump flow rate.

In a 28th aspect according to the 27th aspect the updated pre-dilution pump flow rate and the updated post-dilution pump fluid flow rate are calculated such as to differ from their respective initial values by a same percentage.

In a 29th aspect according to any one of aspects from 20th to 28th the step of calculating the updated set of values comprises maintaining the value of said pre-blood infusion pump flow rate unchanged to its initial set value.

In a 30th aspect according to any one of aspects from 20th to 29th the step of calculating the updated set of values comprises maintaining the value of said patient fluid removal rate unchanged to its initial set value.

In a 31st aspect according to any one of the preceding aspects the control unit is configured to receive an initial set value for the blood pump flow rate and to control said blood pump accordingly, and wherein the step of calculating said updated set of values comprises maintaining the value of the blood pump flow rate unchanged to its initial value.

In a 32nd aspect according to any one of the preceding aspects said control unit is configured to:
 prompt a user to select whether to enter in a dose control mode,
 prompt a user to select a treatment mode,
 receive the user's selections and check whether the selected treatment mode and the dose control mode are conflicting, and
 prevent entering in dose control mode in case of conflict between the selected treatment mode and the selected dose control mode.

In a 33rd aspect according to any one of the preceding aspects herein wherein the control unit is configured to:
 detect if case a treatment mode is selected where use is made of said/a pre-blood pump infusion line for infusing a regional anticoagulant (such as for instance a citrate based solution), and in the affirmative,
 prevent from entering in dose control mode.

In a 34th aspect according to any one of the preceding aspects said flow rate update procedure further comprises:
 comparing the calculated updated set values with respective safety criteria;
 controlling said means for regulating based on said updated set of values of said flow rates if said updated set values fulfill said safety criteria.

In a 35th aspect according to the preceding aspect said flow rate update procedure includes calculating a maximum achievable dose within said safety criteria, and controlling said means for regulating to achieve said maximum achievable dose.

In a 36th aspect according to any one of the preceding aspects the control unit is configured to:
 assess whether said prescribed dose can be reached within said reference time interval,
 calculate a remaining dose as a difference between the prescribed dose and the dose actually achievable within the reference time interval,
 add the remaining dose to the prescribed dose to be achieved in a subsequent time interval.

In a 37th aspect according to any one of the preceding aspects the apparatus further comprises:
 an effluent fluid container connected with an outlet of the effluent line,
 a first scale operative for providing weight information relative to the amount of the fluid collected in the effluent fluid container;
 an infusion fluid container connected with an inlet of said pre-dilution line and/or with an inlet of said post-dilution line;
 a second scale operative for providing weight information relative to the amount of the fluid supplied from the infusion fluid container;
 a dialysis liquid fluid container connected with an inlet of said dialysis fluid line;
 a third scale operative for providing weight information relative to the amount of the fluid supplied from dialysis fluid container;
 the control unit being further configured to:
 receive treatment selection information;
 receive weight information from at least one of the first, second and third scales;
 control, at least at the beginning of the treatment, the flow rate of at least one of the effluent fluid, the infusion fluid, the dialysis fluid by controlling said means for regulating based on said weight information, and said initial set values,
 at time intervals calculate said updated set of values,
 subsequent to each said calculation, control the flow rate of at least one of the effluent fluid, the infusion fluid, the dialysis fluid by controlling said means for regulating based on said weight information, and said updated set of values.

In a 38th aspect according to any one of the preceding aspects the control unit is programmed to allow a user to:
 enter a first value for the prescribed dose (e.g. hourly dose) to be delivered through the entire patient treatment (which can last few days).
 and then
 modify the first value to a second different value of the prescribed dose to be reached during said entire patient treatment.

In a 39th aspect according to the preceding aspect the control unit is configured to calculate, after receipt of said second value, the updated set of values based upon:
 said first value,
 said second value,
 the time at which said second value is entered, and
 the reference time interval.

A 40th aspect relates to a process for controlling an apparatus for extracorporeal treatment of blood, the apparatus being of the type comprising a filtration unit having a primary chamber and a secondary chamber separated by a semi-permeable membrane; a blood withdrawal line connected to an inlet of the primary chamber, and a blood return line connected to an outlet of the primary chamber said blood lines being designed to be connected to a patient cardiovascular system; a blood pump for controlling the flow of blood through the blood lines; an effluent fluid line connected to an outlet of the secondary chamber; at least one fluid line selected in the group comprising: one or more infusion fluid lines connected to one of the blood withdrawal line and the blood return line, and a dialysis fluid line connected to the inlet of the secondary chamber; means for regulating the flow of fluid through said fluid lines. The process, which can for instance be executed by a control unit, includes the steps of:
 set initial values to one or more fluid flow rates selected in the group including a fluid flow rate ($Q_{eff}$) through the effluent line, a fluid flow rate ($Q_{rep}$, $Q_{pbp}$) through the infusion fluid line, a fluid flow rate ($Q_{dial}$) through the dialysis liquid fluid line, and a fluid removal rate ($Q_{pfr}$) from the patient, calculate or receive at least a prescribed dose ($D_{set}$), said prescribed dose being a target mean value of a flow rate to be delivered through an entire patient treatment, execute a flow rate update procedure comprising calculating an updated set of values for one or more of said fluid flow rates based on said prescribed dose ($D_{set}$).

The update set of flow rates is calculated such that during one or more reference time intervals across the treatment time the prescribed dose value is matched.

In a 41$^{st}$ aspect according to the 40$^{th}$ aspect the process comprises the step of controlling said means for regulating the flow of fluid based on said updated set values.

In a 42$^{nd}$ aspect according to the 40$^{th}$ or the 41$^{st}$ aspect, said prescribed dose comprises one flow rate selected in the group including:

effluent dose flow rate ($D_{eff\_set}$), which is the prescribed mean value of the flow rate through the effluent line (13), convective dose flow rate ($D_{conv\_set}$), which is the prescribed mean value of the sum of the flow rates through any infusion fluid line ($Q_{rep}$, $Q_{pbp}$) and the patient fluid removal rate ($Q_{pfr}$), diffusive dose flow rate ($D_{dial\_set}$): which is the prescribed mean value of the flow rate through the dialysis fluid line ($Q_{dial}$), urea dose ($D_{urea\_set}$): which is a prescribed mean value for an estimated urea clearance, clearance dose ($K_{solute\_set}$): which is a prescribed mean value for an estimated clearance for a given solute.

In a 43$^{rd}$ aspect according to any one of 41$^{st}$ or 42$^{nd}$ aspect, the process comprises regularly, e.g. periodically or according to a predetermined time rule, executing said flow update procedure at check points (Ti) during treatment.

In a 44$^{th}$ aspect according to any one of 41$^{st}$ or 42$^{nd}$ or 43$^{rd}$ aspect, the flow update procedure comprises the following steps:

determining a value of the dose delivered ($D_{del}$) over a time interval ($T_{retro}$) preceding a check point ($T_i$);

determining a dose need value ($D_{need}$) based at least on the dose delivered value and on the prescribed dose value ($D_{set}$);

calculating the updated set of values for said fluid flow rates based on said dose need value.

In a 45$^{th}$ aspect according to any one of the preceding aspects from 40$^{th}$ to 44$^{th}$, the step of determining a dose need value at a check point ($T_i$) comprises computing the dose needed to be delivered over a next time period ($T_{prosp}$) following the check point ($T_i$) in order to reach the prescribed dose over a time interval which is the sum of the time interval ($T_{retro}$) preceding check point ($T_i$) and the next time period ($T_{prosp}$).

In a 46$^{th}$ aspect according to the 45$^{th}$ aspect, the dose need value is calculated according to the formula:

$$D\_need = \frac{D\_set \times T\_prosp + (D\_set - D\_del) \times T\_retro}{T\_prosp}$$

where:

$D_{del}$ is the dose delivered over a time interval ($T_{retro}$) preceding a check point ($T_i$);

$D_{need}$ is the dose need value, $T_{retro}$ is a time interval preceding check point ($T_i$), $T_{prosp}$ is the next time period following the check point ($T_i$), $D_{set}$ is the prescribed dose value over the reference time interval which is the sum of the time interval ($T_{retro}$) preceding check point ($T_i$) and the next time period ($T_{prosp}$).

In a 47$^{th}$ aspect according to any one of the preceding aspects from the 40$^{th}$ to the 46$^{th}$, the process includes determining an effective portion ($T_{eff}$) of said next time period In a 48$^{th}$ aspect according to the 47$^{th}$ aspect the process comprises calculating a corrected dose value ($D_{computed}$) as follows:

$$D\_computed = D\_need \times \frac{T\_prosp}{T\_eff}$$

In a 49$^{th}$ aspect according to the 48$^{th}$ aspect, the process comprises executing the flow update procedure also taking into account for said effective portion ($T_{eff}$) to be expected over the next time period ($T_{prosp}$) by calculating the updated set of values for said fluid flow rates based on said corrected dose value ($D_{computed}$).

In a 50$^{th}$ aspect according to any one of the preceding aspects from 40$^{th}$ to 49$^{th}$ the process comprises allowing selection (for instance through a user interface) of one of a plurality of treatment modes, said treatment modes comprising at least two of hemodialysis (HD), hemofiltration with pre-dilution ($HF_{pre}$), hemofiltration with post-dilution ($HF_{post}$), hemofiltration with both pre-dilution and post-dilution ($HF_{pre-post}$), hemodiafiltration with pre-dilution ($HDF_{pre}$), hemodiafiltration with post-dilution ($HDF_{post}$), hemodiafiltration with both pre-dilution and post-dilution ($HDF_{pre-post}$), ultrafiltration (UF), and to control the means for regulating based on the treatment mode selection.

In an 51$^{st}$ aspect according to any one of aspects from 42$^{nd}$ to 50$^{th}$, wherein the process comprises allowing selection of one or more dose options (for instance through a user interface), each dose option specifying a respective one of said prescribed doses which a user can select to be the dose placed under control.

In a 52$^{nd}$ aspect to the 51$^{st}$ aspect the calculation of said updated set of flow rate value or values is also based on said treatment selection and on said dose option selection. In other words depending upon the selected treatment, only specific pumps are under control (for instance if the treatment is HF, then the dialysis pump is not used at all), and depending upon the dose option and set dose value $D_{set}$, the process updates at time intervals the set of flow rates accordingly.

In a 53$^{rd}$ aspect according to any one of the preceding aspects from 40$^{th}$ to 52$^{nd}$, the process executes said flow rate update procedure only if the user selects to enter in the dose control mode e.g. through an appropriate command on the user interface of the apparatus.

In a 54$^{th}$ aspect according to the 53$^{rd}$ aspect the process comprises:

displaying on the user interface an indicium prompting a user to enter said initial set values of said fluid flow rates, receiving said initial set values, detecting if the user selects said dose control mode, and if the user selects to enter in the dose control mode, calculating the prescribed dose based on said initial set values.

In a 55$^{th}$ aspect according to the 53$^{rd}$ aspect the process comprises:
detecting if the user selects to enter in dose control mode,
if the user selects to enter in the dose control mode, displaying an indicium prompting a user to enter the prescribed dose, and optionally
calculating said initial values of said flow rates based on said prescribed dose.

In a 56$^{th}$ aspect according to any one of the preceding aspects, said flow rate update procedure comprises:
displaying on a user interface said calculated updated set of values for said flow rates, prompting user to confirm said updated set of values for said flow rates.

In a 57$^{th}$ aspect according to the 56$^{th}$ aspect the update procedure includes the steps of checking if the user approved the updated set of flow rate values and, only if the user has approved the updated set of values, controlling said means based on said updated set of values for said flow rates. In other words the updated values for the flow rates are implemented only after approval from the user.

In an 58$^{th}$ aspect according to any one of the preceding aspects, the process comprises:
starting a treatment controlling said means for regulating based on said initial set of flow rates; and
at time periods executing said flow rate update procedure.

In an 59$^{th}$ aspect according to any one of the preceding aspects from 51$^{st}$ to 57$^{th}$, the flow-rate update procedure is made before treatment start and at time intervals after treatment start.

In a 60$^{th}$ aspect according to any one of the preceding aspects from 40$^{th}$ to 59$^{th}$ the step of calculating the updated set of values comprises calculating an updated infusion pump flow rate and an updated dialysis pump flow rate. The updated infusion pump flow rate and updated dialysis pump flow rate can differ from their respective initial values by a same percentage or, alternatively by different percentages. In an option it is possible changing value of one of the infusion pump flow rate and the dialysis pump flow rate, without changing the value of the other.

In a 61$^{st}$ aspect according to any one of aspects from 40$^{th}$ to 60$^{th}$ calculating an updated infusion pump flow rate comprises calculating an updated pre-dilution pump flow rate and an updated post-dilution pump flow rate. The updated pre-dilution pump flow rate and the updated post-dilution pump fluid flow rate are calculated such as to differ from their respective initial values by a same percentage. Alternatively, said pre-blood infusion pump flow rate can be maintained unchanged to its initial set value.

In a 62$^{nd}$ aspect according to any one of aspects from 40$^{th}$ to 61$^{st}$ the step of calculating the updated set of values comprises maintaining the value of said patient fluid removal rate unchanged to its initial set value.

In a 63$^{rd}$ aspect according to any one of aspects from 40$^{th}$ to 62$^{nd}$ the step of calculating the updated set of values comprises receive an initial set value for the blood pump flow rate and to control said blood pump accordingly, and wherein the step of calculating said updated set of values comprises maintaining the value of the blood pump flow rate unchanged to its initial value.

In a 64$^{th}$ aspect according to any one of the preceding aspects from 40$^{th}$ to 62$^{nd}$ the process comprises:
prompting a user to select whether to enter in a dose control mode,
prompting a user to select a treatment mode,
receiving the user's selections and checking whether the selected treatment mode and the dose control mode are conflicting, and
preventing from entering in dose control mode in case of conflict between the selected treatment mode and the selected dose control mode.

In a 65$^{th}$ aspect according to any one of the preceding aspects from 40$^{th}$ to 64$^{th}$ the process comprises detecting if a treatment mode is selected where use is made of said/a pre-blood pump infusion line for infusing a regional anticoagulant (such as for instance a citrate based solution), and in the affirmative, preventing from entering in dose control mode.

In a 66$^{th}$ aspect according to any one of the preceding aspects from 40$^{th}$ to 65$^{th}$ said flow rate update procedure further comprises:
comparing the calculated updated set values with respective safety criteria;
controlling said means for regulating based on said updated set of values of said flow rates if said updated set values fulfill said safety criteria.

In a 67$^{th}$ aspect according to any one of the preceding aspects from 40$^{th}$ to 66$^{th}$ said flow rate update procedure further comprises:
calculating a maximum achievable dose within said safety criteria, and controlling said means for regulating to achieve said maximum achievable dose.

In a 68$^{th}$ aspect according to any one of the preceding aspects from 40$^{th}$ to 67$^{th}$ said process further comprises:
assessing whether said prescribed dose can be reached within said reference time interval,
calculating a remaining dose as a difference between the prescribed dose and the dose actually achievable within the reference time interval,
adding the remaining dose to the prescribed dose to be achieved in a subsequent time interval.

In a 69$^{th}$ aspect according to any one of the preceding aspects from 40$^{th}$ to 68$^{th}$ said flow rate update procedure further comprises:
entering a first value for the prescribed dose to be maintained across the entire treatment time and then
modifying the first value to a second different value of the prescribed dose to be maintained across the entire treatment time.

In a 70$^{th}$ aspect according to the preceding aspect wherein, after receipt of said second value, the updated set of values is calculated based upon:
said first value,
said second value,
the time at which said second value is entered, and
the reference time interval.

In a 71$^{st}$ aspect a data carrier including instructions executable by a control unit of a blood treatment apparatus is provided. The instructions are configured such that, when executed by the control unit, they cause execution of the process according to any one of the preceding aspects from 40$^{th}$ to 70$^{th}$.

In a 72$^{nd}$ aspect according to the preceding aspect the data carrier can be any support suitable for storing data, such as by way of non-limiting example: a RAM, a ROM, an EPROM, an optical or a magnetic disc, an electromagnetic wave, a mass memory storage device such as an Hard Disk or a flash memory bank.

DESCRIPTION OF THE DRAWINGS

Aspects of the invention are shown in the attached drawings, which are provided by way of non-limiting example, wherein.

DETAILED DESCRIPTION

Figure 1:
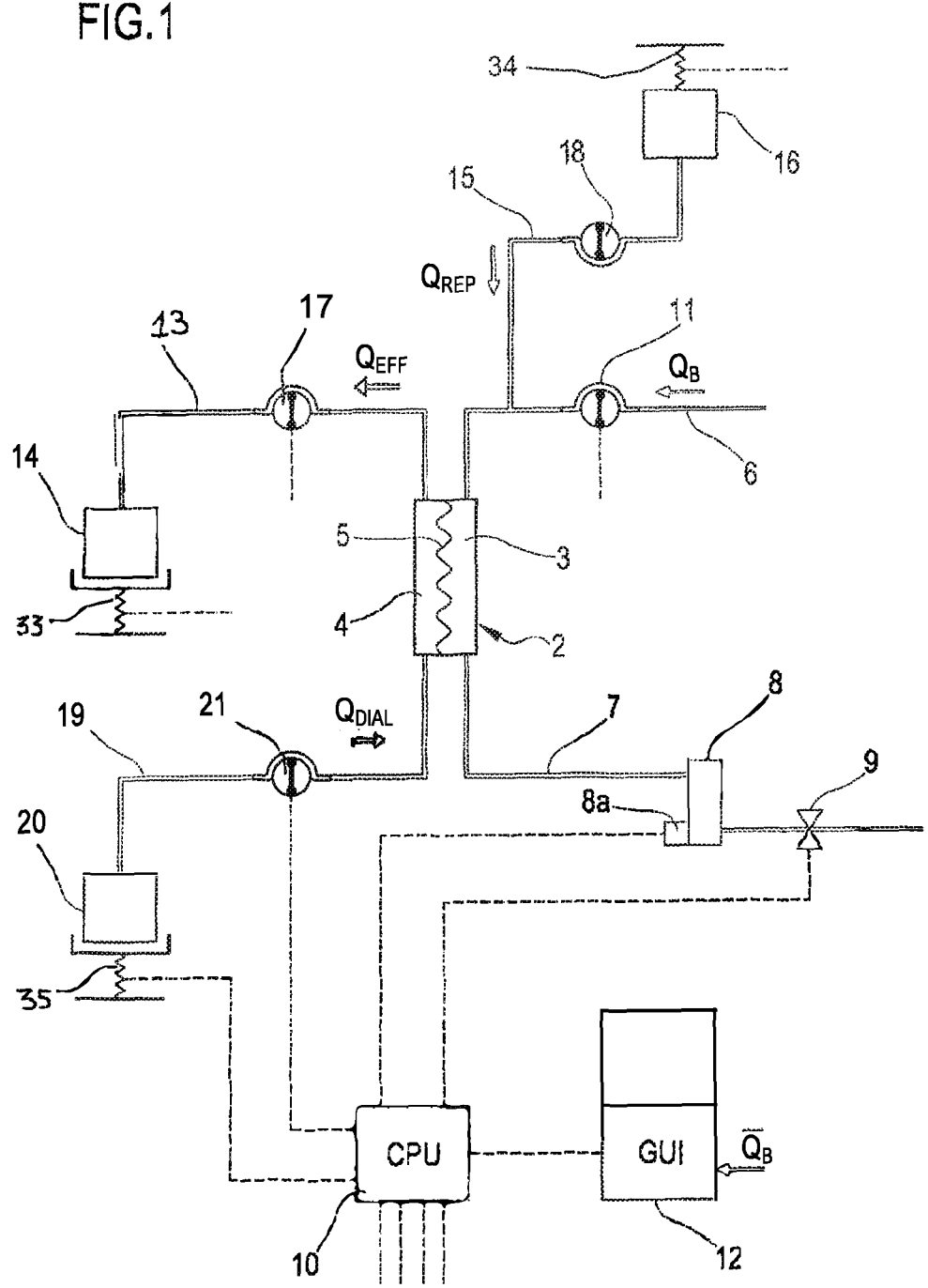
FIG. 1 shows a schematic diagram of a blood treatment apparatus according to one aspect of the invention.
Figure 2:
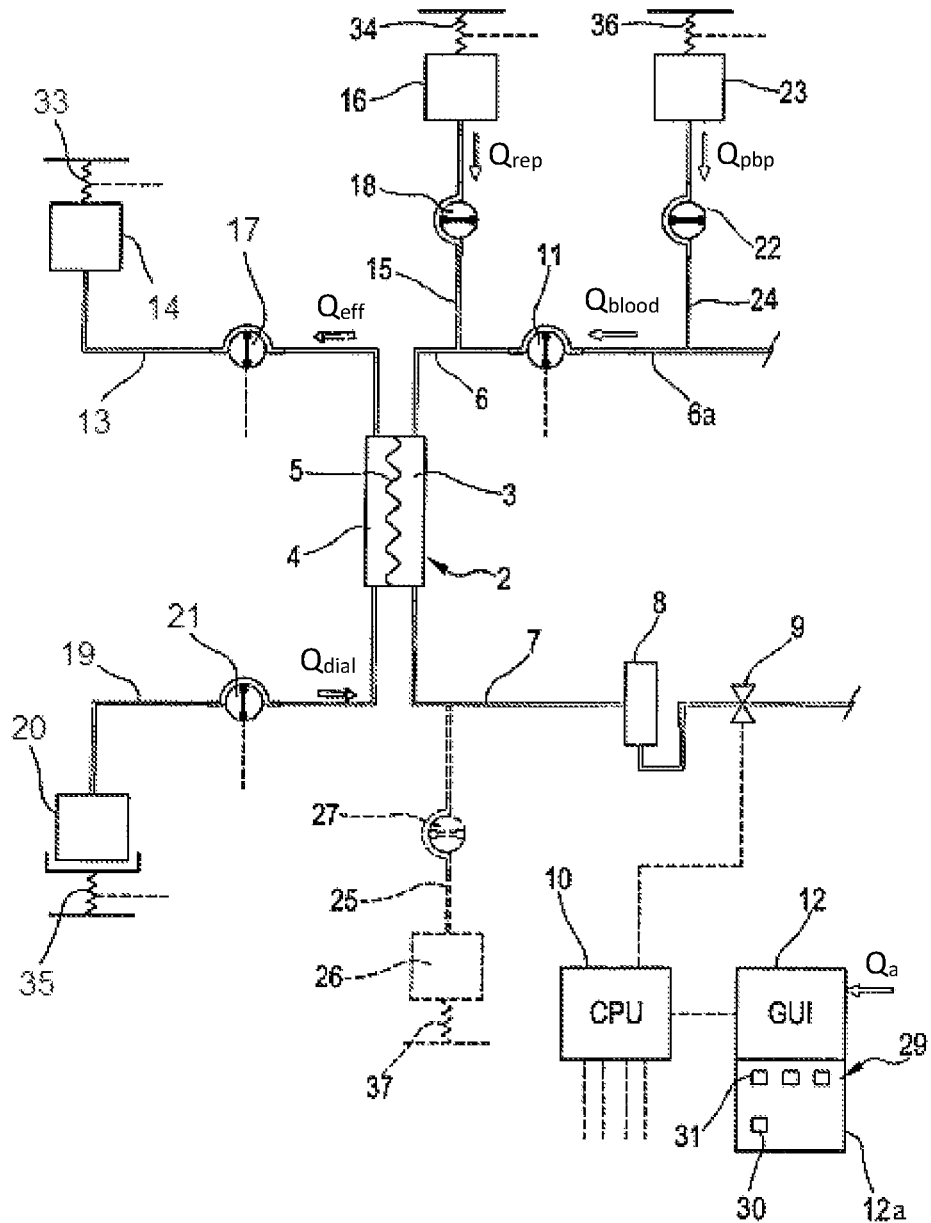
FIG. 2 shows a schematic diagram of an alternative embodiment of a blood treatment apparatus according to another aspect of the invention.

FIGS. 1 and 2 show two exemplifying embodiments of apparatuses for extracorporeal treatment of blood. Note that same components present in both figures are identified by same reference numerals. FIG. 1 shows an apparatus 1 which is designed for delivering any one of treatments like hemodialysis, hemofiltration, hemodiafiltration, ultrafiltration. In fact, the apparatus 1 comprises a filtration unit 2 having a primary chamber 3 and a secondary chamber 4 separated by a semi-permeable membrane 5; depending upon the treatment the membrane of the filtration unit may be selected to have different properties and performances.

A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or other access device (not shown) which is then placed in fluid communication with the patient vascular system, such that blood can be withdrawn through the blood withdrawal line, flown through the primary chamber and then returned to the patient's vascular system through the blood return line. An air separator, such as a bubble trap 8 can be present on the blood return line; moreover, a safety clamp 9 controlled by a control unit 10 can be present on the blood return line downstream the bubble trap 8. A bubble sensor 8a, for instance associated to the bubble trap 8 or coupled to a portion of the line 7 between bubble trap 8 and clamp 9 can be present: if present, the bubble sensor is connected to the control unit 10 and sends to the control unit signals for the control unit to cause closure of the clamp 9 in case one or more bubbles are detected.

As shown in FIG. 1, the blood flow through the blood lines is controlled by a blood pump 11, for instance a peristaltic blood pump, acting either on the blood withdrawal line (as shown in FIG. 1) or on the blood return line. An operator can enter a set value for the blood flow rate $Q_B$ through a user interface 12 and the control unit 10, during treatment, is configured to control the blood pump based on the set blood flow rate. The control unit can comprise a digital processor (CPU) and necessary memory (or memories), an analogical type circuit, or a combination thereof. In the course of the present description it is indicated that the control unit is "configured" or "programmed" to execute certain steps: this can be achieved in practice by any means which allow configuring or programming the control unit. For instance, in case of a control unit comprising one or more CPUs, a program can be stored in an appropriate memory containing instructions which, when executed by the control unit, cause the control unit to execute the steps herein described. Alternatively, if the control unit is of an analogical type, then the circuitry of the control unit can be designed to include circuitry configured in use to execute the steps herein disclosed.

Going back to FIG. 1, an effluent fluid line 13 is connected, at one end, to an outlet of the secondary chamber 4 and, at another end, to an effluent fluid container 14 collecting the fluid extracted from the secondary chamber. The embodiment of FIG. 1 also presents a pre-dilution fluid line 15 connected to the blood withdrawal line: this line 15 supplies replacement fluid from an infusion fluid container 16 connected at one end of the pre-dilution fluid line. Note that alternatively to the pre-dilution fluid line the apparatus of FIG. 1 could include a post-dilution fluid line (not shown in FIG. 1) connecting an infusion fluid container to the blood return line. Finally, as a further alternative (not shown in FIG. 1) the apparatus of FIG. 1 could include both a pre-dilution and a post infusion fluid line: in this case each infusion fluid line can be connected to a respective infusion fluid container or the two infusion fluid lines could receive infusion fluid from a same infusion fluid container. An effluent fluid pump 17 operates on the effluent fluid line under the control of said control unit 10 to regulate the flow rate $Q_{eff}$ across the effluent fluid line. Furthermore, an infusion pump 18 operates on the infusion line 15 to regulate the flow rate $Q_{rep}$ through the infusion line. Note that in case of two infusion lines (pre-dilution and post-dilution) each infusion line can cooperate with a respective infusion pump. The apparatus of FIG. 1, further includes a dialysis fluid line 19 connected at one end with a dialysis fluid container 20 and at its other end with the inlet of the secondary chamber 4 of the filtration unit. A dialysis liquid pump 21 works on the dialysis liquid fluid line under the control of said control unit 10, to supply fluid from the dialysis liquid container to the secondary chamber at a flow rate $Q_{dial}$.

The dialysis fluid pump 21, the infusion fluid pump 15 and the effluent fluid pump 17 are part of means for regulating the flow of fluid through the respective lines and, as mentioned, are operatively connected to the control unit 10 which controls the pumps as it will be in detail disclosed herein below. The control unit 10 is also connected to the user interface 12, for instance a graphic user interface, which receives operator's inputs and displays the apparatus outputs. For instance, the graphic user interface 12 can include a touch screen, a display screen and hard keys for entering user's inputs or a combination thereof.

The embodiment of FIG. 2 shows an alternative apparatus 1 where the same components described for the embodiment of FIG. 1 are also presents and are identified by same reference numerals and thus not described again. Additionally, the apparatus 1 shown in FIG. 2 may present a further infusion line 22 connected, at one end, with a portion 6a of the blood withdrawal line 6 positioned upstream the blood pump 11 and, at its other end, with a further infusion fluid container 23, which for instance may contain a drug, or a regional anticoagulant such as a citrate solution, or a nutrients solution or other. This further infusion line is herein referred to as pre-blood pump infusion line 22. The means for regulating comprises a pump 22, for instance a peristaltic pump controlled by control unit 10, acting on a segment of the pre-blood pump infusion line to regulate a pre-blood pump infusion rate $Q_{pbp}$.

The apparatus of FIG. 2, may also present a post-dilution line 25 (represented with dashed line) connected at one end with a further container 26 of infusion liquid and connected at its other end with the blood return line 7. A further pump 27, for instance a peristaltic pump, may act under the control of control unit 10 on the post-dilution line 25 and thus also be part of said means for regulating the flow through the fluid lines.

Of course other configurations could be possible and the solutions of FIGS. 1 and 2 are merely intended for exemplifying purpose.

Dose Definitions

In the present specification, dose is a flow rate or to a combination of flow rates. For example, one of the following magnitudes can be used as dose for the purpose of the present invention:

effluent dose $D_{\it eff}$: the flow rate across the effluent line $Q_{\it eff}$, convective dose $D_{conv}$: the sum of the flow rates $Q_{rep}+Q_{pbp}+Q_{pfr}$, where $Q_{pfr}$ represents the patient fluid removal rate, $Q_{rep}$ is the flow rate through the infusion line or lines connected directly to the patient or connected to the blood circuit downstream the blood pump and $Q_{pbp}$ is the flow rate through the pre-blood pump infusion line, diffusive dose $D_{dial}$: the flow rate $Q_{dial}$ of fluid supplied to the filtration unit secondary chamber, urea dose $D_{urea}$: estimated urea clearance; note that a first approximated expression assumes that filter Urea clearance is more or less identical to effluent flow rate $Q_{\it eff}$; alternatively a urea monitor could be placed on the effluent line in order to measure an actual value of the urea clearance; in a further alternative, an estimate of urea clearance more accurate than $Q_{\it eff}$, especially when operating with large flow rates or small filters (paediatric conditions), can be provided by the following equations:

a) for purely diffusive mode (where there is no infusion of replacement fluid and where the patient fluid removal rate is zero or substantially zero) and counter-courant flow configuration (fluids in the chambers of the filtration unit 2 are countercurrent):

$$Z = \frac{Qpw_{inlet}}{Qdial}$$

$$NT = \frac{S/RT}{Qpw_{inlet}}$$

$$K(Qpw_{inlet}, Qdial) = Qpw_{inlet} \times \frac{\exp[NT \times (1-Z)] - 1}{\exp[NT \times (1-Z)] - Z} \text{ if } Z \neq 1$$

$$K(Qpw_{inlet}, Qdial) = Qpw_{inlet} \times \frac{NT}{NT + 1} \text{ if } Z = 1$$

where: S (effective surface area) is dependent on the hemodialyzer (as filtration unit 2) in use; RT is total mass transfer resistance dependent of the hemodialyzer in use (membrane properties, filter design) and the solute of interest; and $Qpw_{inlet}$ is the plasma water flow rate at the inlet of the filtration unit 2.

b) in case of presence of both $Q_{dial}$ and of one or more infusions of fluid, then:

$$\gamma = \exp\left(\frac{SC \times Qfil}{S/RT}\right) - 1$$

$$f = \left(\frac{Qpw_{inlet} - SC \times Qfil}{Qpw_{inlet}} \times \frac{Qdial + SC \times Qfil}{Qdial}\right)^{1/\gamma}$$

-continued $$K(Qpw_{inlet}, Qdial, Qfil) = \frac{Qpw_{inlet} \times Qdial - f \times (Qpw_{inlet} - SC \times Qfil) \times (Qdial + SC \times Qfil)}{Qdial - f \times (Qpw_{inlet} - SC \times Qfil)}$$

where: S (effective surface area) is dependent on the hemodialyzer use; $Q_{fil}=Q_{pbp}+Q_{rep}+Q_{pfr}$ (again, $Q_{pfr}$ represents the patient fluid removal rate, $Q_{rep}$ is the flow rate through the infusion line or lines connected directly to the patient or connected to the blood circuit downstream the blood pump and $Q_{pbp}$ is the flow rate through the pre-blood pump infusion line); and $Qpw_{inlet}$ is the plasma water flow rate at the inlet of the filtration unit 2.

clearance dose: an estimated clearance for a given solute; for certain solutes a first approximated expression assumes that filter solute clearance is more or less identical to effluent flow rate $Q_{\it eff}$; alternatively solute clearance can be estimated as function of all flow settings and of dialyzer/filter 2 related parameters; alternatively appropriate sensors could be placed to measure conductivity or concentration and thereby allow calculation of an actual clearance for a given solute (e.g. sodium), for instance using one of the methods described in EP patent n.0547025 or EP patent n.0658352 or EP patent n.0920887. In a further alternative the equations of above paragraphs a) and b) as described for the urea clearance could be used with RT adapted to take into account the specific solute.

When referring to any one of the above defined doses a distinction is also over:

prescribed dose, which is represented by the target mean values of flow rate(s) to be delivered over the patient treatment or other reference time interval; a prescribed dose for one of the above listed doses (prescribed effluent dose $D_{\it eff\_set}$, prescribed convective dose $D_{conv\_set}$, prescribed dialysis dose $D_{dial\_set}$, prescribed urea dose $D_{urea\_set}$, prescribed clearance dose $K_{solute\_set}$) shall normally be defined or calculated at the treatment start;

achieved dose $D_{del}$, which is the average dose actually delivered over a certain interval of reference Ti, current or instantaneous dose, which is the actual dose the blood treatment apparatus with the current settings is instantaneously delivering at time Ti.

In the course of the following description reference will be made to the above dose definitions which are relating to doses not normalized to patient body weight (BW) or patient surface area (A). Of course the same principles and formulas below described could be normalized to body weight or patient surface area by dividing the dose value by either body weight BW or surface area A.

Normalized Dose=Dose/BW or

NDose=Dose/A×1.73 (when normalised to a 1.73 m² surface area patient)

Furthermore, the above defined doses could be corrected to take into account the predilution effect, when a fluid replacement line is present upstream the treatment unit, such as lines 15 and 22 in the enclosed drawings. Each of the above defined doses could be corrected multiplying the dose value times a dilution factor $F_{dilution}$:

Dose$_{corr\_xxx}=F_{dilution}\times$Dose$_{xxx}$ (with xxx=eff, conv, dial, etc)

The dilution factor $F_{dilution}$ can be defined according to one of the following:

Blood dilution factor:

$$Fdilution_{blood} = \frac{Qb}{Qb + Qpre}$$

Plasma dilution factor:

$$Fdilution_{plasma} = \frac{Qp}{Qp + Qpre} = \frac{(1 - Hct) \times Qb}{(1 - Hct) \times Qb + Qpre}$$

Plasma water dilution factor:

$$Fdilution_{pw} = \frac{Qpw}{Qpw + Qpre} = \frac{(1 - Hct) \times Fp \times Qb}{(1 - Hct) \times Fp \times Qb + Qpre}$$

Where $Q_{pre}$ is the total predilution infusion rate (where two infusion lines are present upstream the treatment unit, as lines 15 and 22, $Q_{pre}$ combines PBP infusion 15 and pre-replacement infusion 22)

$Q_b$: blood flow
$Q_p$: plasma flow rate
$Q_{pw}$: plasma water flow rate
Hct: haematocrit
$F_p$: plasma water fraction, which is a function of total protein concentration (typical value Fp=0.95)

In practice, the effluent dose corrected for the predilution effect would be: $Dose_{corr\_eff} = F_{dilution} \times Dose_{\_eff}$.

As to the urea dose, a first expression assumes that filter Urea clearance (K_urea) is more or less identical to effluent flow rate. As urea is distributed in whole blood and can transfer quickly through the red blood cells membrane, the most relevant correction factor to consider for predilution shall refer to whole blood. Accordingly:

$$Dose\_urea = Fdilution_{blood} \times K\_urea = \frac{Qb}{Qb + Qpre} \times Qeff$$

Of course, more sophisticated equations could provide for a more accurate estimate of K_urea than Qeff, especially when operating with large flow rates or small filters (pediatric conditions).

As to the clearance dose an expression of dose based on the clearance of a given solute can be considered. $F_{dilution}$ factor shall be selected according to the solute distribution and ability to move through red blood cell (RBC) membrane (example: creatinin has slow diffusion through RBC, thus plasma dilution factor $F_{dilution\_plasma}$ should be used). Solute clearance to be estimated through equations like those referred to Urea clearance (see above), using the relevant mass transfer parameters for selected filter and solute.

Initial Setting

Depending upon the design choice, the prescribed dose can be either entered by the operator at the beginning of the treatment or it can be calculated at the beginning of the treatment based on initial set values for one or more flow rates through the lines of the blood treatment machine.

Figure 3:
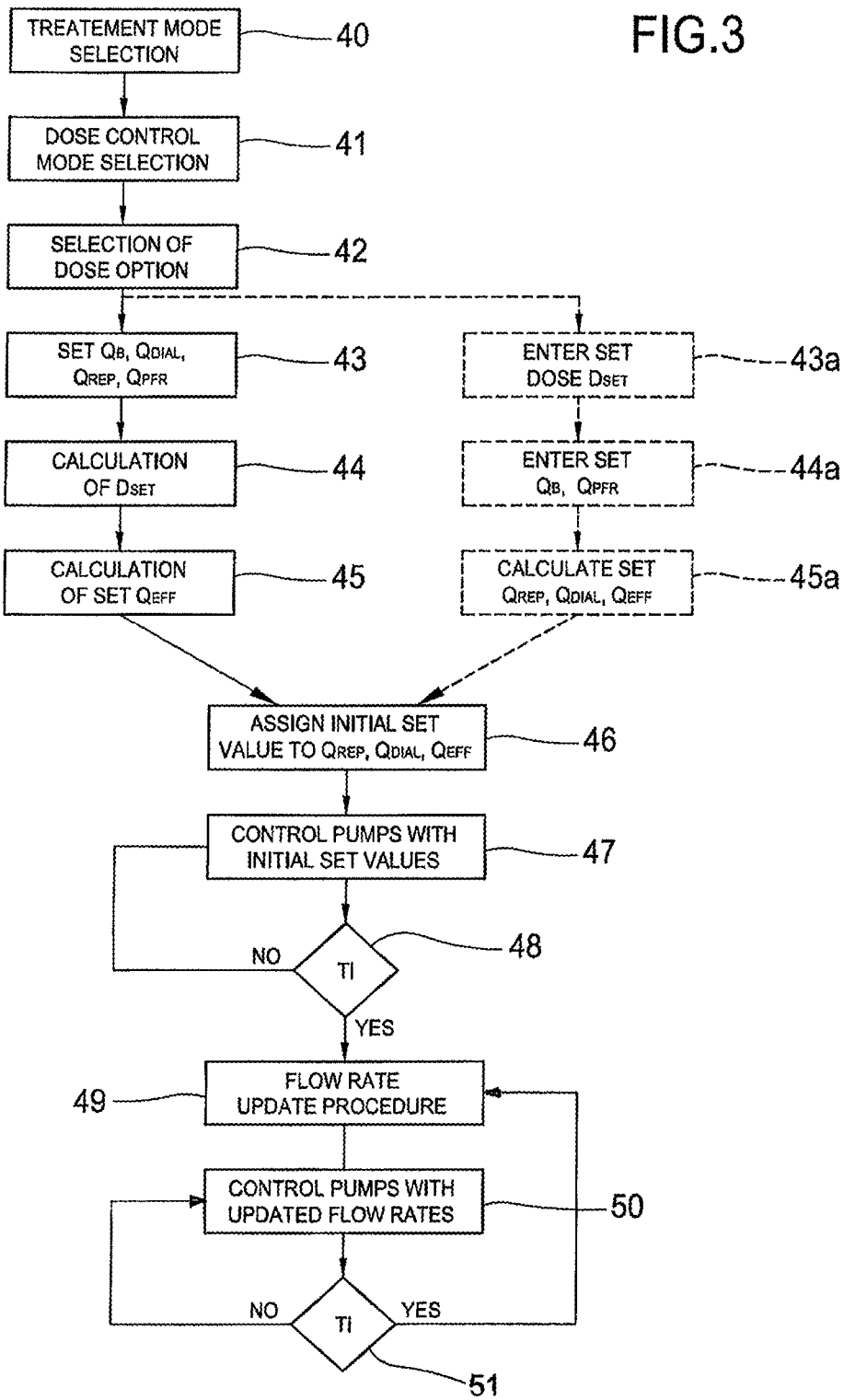
FIG. 3 shows a block diagram of a procedure executable by a control unit according to a further aspect of the invention.

In one aspect, the control unit 10 is configured to display on the screen 12*a* of the user interface 12 a number of indicia, including: an indicium 30 prompting a user to select whether to enter in a "dose control mode", one or more indicia 31 prompting the user to select among a plurality of "treatment modes" such as by way of non-limiting example among one or more of hemodialysis (hereinafter HD), hemofiltration with pre-dilution (hereinafter $HF_{pre}$), hemofiltration with post-dilution (hereinafter $HF_{post}$), hemofiltration with both pre-dilution and post-dilution (hereinafter $HF_{pre-post}$), hemodiafiltration with pre-dilution (hereinafter $HDF_{pre}$), hemodiafiltration with post-dilution (hereinafter $HDF_{post}$), hemodiafiltration with both pre-dilution and post-dilution (hereinafter $HDF_{pre-post}$), ultrafiltration (hereinafter UF), etcetera. In practice, if the user interface comprises a touch screen 29, the indicia 30 and 31 can be selected touch sensitive areas or buttons on the touch screen surface. The control unit may be configured to allow first selection of the treatment and then selection as to whether or not entering in "dose control mode". Of course the opposite sequence can be possible too. An exemplifying sequence of steps that the control unit is configured or programmed to execute is shown in FIG. 3: as a first step 40 the user is allowed to select the "treatment mode" and then he is allowed to select to enter in "dose control mode" at step 41. If the user selects to enter in "dose control mode", then the control unit may be configured to proceed according to different alternative solutions. In a first alternative shown in FIG. 3, the control unit 10 can be configured to display on the user interface an indicium prompting (step 42) a user to select a dose option (e.g. effluent dose $Q_{eff}$, convective dose $Q_{rep}+Q_{pbp}+Q_{pfr}$, diffusive dose $Q_{dial}$, urea dose, clearance dose) and an indicium prompting the user to enter initial set values of fluid flow rates, which depending upon the treatment mode may be one or more of the flow rates through lines 13, 15, 19, 21 and 25. If for instance the selected treatment mode is HDF (hemodialfiltration), then the user may be requested to enter (step 43) the set flow rate values for 3 of: set flow rate through the dialysis fluid line, set flow rate through the infusion line, patient fluid removal rate, set flow rate through the effluent line; the fourth set flow rate value is normally calculated by the control unit as the algebraic sum of the rates just mentioned (step 45). If the selected treatment is HD (pure hemodialysis) or HF (hemofiltration), then the user will be requested to enter one set value less than in HDF. At this stage (step 43) the user is also typically requested to enter the blood pump flow rate $Q_B$. Once the user enters said flow rate values, the control unit is configured to receive said initial set values and to calculate the prescribed dose (step 44) based on said initial set values and on the selected dose option. Note the sequence of steps 44 and 45 is merely exemplificative and could be reversed.

EXAMPLE 1—FIG. 3

First alternative: the user enters the set flow rates through 3 of the 4 lines and the control unit calculates the set average dose and the set value for the 4$^{th}$ flow rate based on the 3 entered flow rate set values.

Assuming the user enters the following set values (step 42):

$Q_B$=200 ml/min
$Q_{dial}$=2000 ml/h
$Q_{rep}$=1000 ml/h
$Q_{pfr}$=100 ml/h

Then, the control unit would calculate the set value for the effluent line (step 45):

$Q_{eff} = Q_{dial} + Q_{rep} + Q_{pfr} = 3100$ ml/h

The above value for $Q_{eff}$ would then be assigned as (step 44) the prescribed hourly effluent dose $D_{set\ eff}$ to be delivered through the entire patient treatment which can last few days.

In a second alternative (the differences with respect to the first alternative are represented in FIG. 3 with dashed lines), after steps 40 and 41, the control unit can be configured to display on the user interface an indicium prompting a user to select the dose option (step 42) and an indicium prompting (step 43*a*) to enter: the prescribed dose for the selected dose option, the blood pump flow rate $Q_B$ and of the patient fluid removal rate $Q_{pfr}$ (step 44*a*). For instance, if the user entered in dose control mode and selected the effluent fluid dose as dose option, then the control unit may be programmed to request the user to enter the prescribed dose $D_{set\_eff}$, the value of the blood pump flow rate $Q_B$ and of the patient fluid removal rate $Q_{pfr}$. The control unit can then be configured to calculate the set values of the other flow rates ($Q_{dial}$, $Q_{rep}$, $Q_{eff}$) at step 45*a*.

Assuming the user enters the following values:

$D_{set\_eff}$=Dose effluent=3200 ml/h as prescribed dose of effluent to be kept as mean value across the entire treatment.

$Q_B$=200 ml/min $Q_{pfr}$=100 ml/h

Then, the control unit would calculate the set values for flow rates through the various lines (step 45*a*) as a function of the set dose, of the patient fluid removal rate and of a pre-determined algorithm. Using the above figures, the control unit would set the effluent flow rate to an initial set value $Q_{eff}$=3200 ml/h and then determine the dialysis fluid flow initial set value $Q_{dial}$ and the infusion flow initial set value $Q_{rep}$, dividing, e.g. in two equal parts, the difference $Q_{effluent}-Q_{pfr}$, thus obtaining 1550 ml/h for each of $Q_{dial}$ and $Q_{rep}$ (of course other pre-stored rules could be applied).

In a third alternative (not shown in FIG. 3), the control unit can be configured perform steps 40, 41 and 42 and then to display on the user interface an indicium prompting a user to enter the prescribed dose value for the selected dose option as well as set values for the blood flow rate, the patient fluid removal rate and, depending on the selected treatment, for one or more of the infusion fluid flow rate (or rates) and the dialysis fluid flow rate.

Irrespective of which one of the above alternatives is followed, the control unit 10 is configured to assign set initial values to one or more fluid flow rates (step 46 in FIG. 3) selected in the group including a fluid flow rate through the effluent line, a fluid flow rate through pre-dilution fluid line, a fluid flow rate through the post-dilution fluid line and a dialysis liquid fluid line. In case of an apparatus of the type of FIG. 1 or 2, and if the selected treatment is e.g. HDF$_{pre}$, the control unit assigns initial set values for the dialysis fluid flow rate, the infusion fluid flow rate, and the patient fluid removal rate. These initial set flow rates are used by the control unit to control the means for regulating (e.g. pumps 17, 18, 21 referring to FIG. 1) during an initial period from treatment start (step 47).

Flow Rate Update Procedure

The control unit is also configured to periodically (e.g. at check intervals of 2 or 3 or 4 hours after start of the treatment, see step 48) execute a flow rate update procedure (step 49). Note that the control unit can also be configured to run a first update procedure immediately before start of the treatment. Once the flow rate update procedure has been completed the various pumps are controlled with the new and updated flow rates (step 50) until a next time interval has passed. When a further time interval Ti has passed (step 51) a new flow rate update procedure (step 49) is run and new updated values for controlling the pumps calculated (step 50). The loop of steps 49, 50, 51 is then cyclically repeated.

The update procedure (step 49) is designed in order to make sure that the prescribed dose for the selected dose option (e.g. the effluent dose $D_{eff}$) is actually achieved across a reference time interval, as it will explained herein below.

The reference time interval may be set at 48 hours and a plurality of check points separated by check intervals are provided during the reference time; at each check point the control unit is configured to run the flow rate update procedure.

More in detail the control unit can be configured to regularly execute, e.g. periodically, at check points Ti during treatment, a flow rate update procedure (step 49) comprising the following steps:

determining the value of the dose delivered $D_{del}$ over a time interval preceding check point $T_i$; in case for instance the dose is the effluent fluid dose $D_{del\_eff}$, the actually delivered effluent dose can be obtained by measuring the fluid collected in the effluent container 14;

determining a dose need value $D_{need}$ based at least on the dose delivered value and on the prescribed dose value;

calculating an updated set of values for said fluid flow rates based on said dose need value: if the system detects that the delivered dose is below the expected fraction of dose necessary to achieve the prescribed dose within or at the prescribed time interval then at least one of the updated set of values will be adjusted to a value higher than its initial value.

The above update procedure can be iteratively repeated at time intervals.

Figure 5:
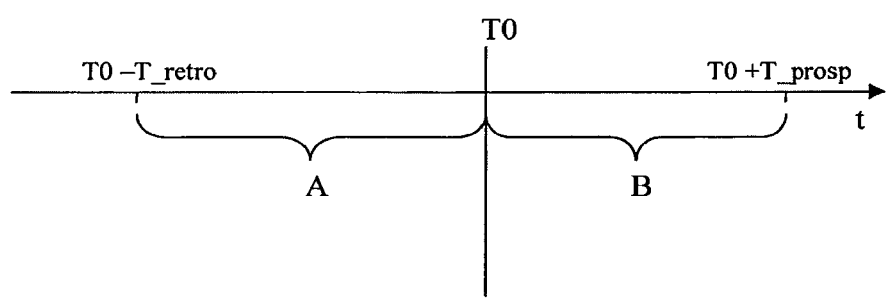
FIG. 5 shows a representation of adjacent time intervals in an update procedure.

Below a short description of an algorithm for iterative adjustments of the flow rate setting in order to achieve the set dose across a reference time. In below example, which makes reference to FIG. 5, the update procedure is executed at a check point $T_0$ making reference to a reference time interval $T_{prosp}$ successive in time to $T_0$ and to a time interval $T_{retro}$ antecedent in time with respect to $T_0$. In FIG. 5, with "A" it is represented the time window $T_0$-$T_{retro}$ and with "B" the next time window $T_0$-$T_{prosp}$.

Typical values for time windows are: $T_{retro}$=$T_{prosp}$=24 hours. Thus the time interval of reference is basically 48 hours as mentioned above.

The computations steps, which can be periodically re-iterated, are the following:

compute the dose delivered ($D_{del}$) retrospectively over time period $T_{retro}$ according to the cumulated volumes over the period; the fact the actual dose may be below its expected value may be caused by several factors, such as apparatus down times due to bag changes, disposable set changes or other operator's actions, warnings and/or alarm conditions, pumps delivery inaccuracies and so on;

compute the dose needed to be delivered over $T_{prosp}$ period in order to reach the set dose over time period $T_{retro}+T_{prosp}$:

$$D\_need = \frac{D\_set \times T\_prosp + (D\_set - D\_del) \times T\_retro}{T\_prosp}$$

Compute the updated set values for flow rates needed to deliver the $D_{need}$ over $T_{prosp}$ time period.

In the calculation of the updated set of values, the control unit can additionally be programmed to estimate an effective portion $T_{eff}$ of said next time period $T_{prosp}$ during which treatment will be actually delivered to the patient. The estimation of the effective portion $T_{eff}$ of the remaining treatment time allows the control unit to account for possible down times, or period of no treatment delivery (bag changes, disposable changes, alarms, etc. that may cause temporary stop of treatment delivery as either the blood flow of the flow in one or more fluid lines is interrupted) which may occur in the future and which may, however, be statistically forecasted with a certain degree of accuracy. Thus, the control unit can be configured to also consider and estimate the effective run time of pumps $T_{eff}$ to be expected over the coming time period $T_{prosp}$. The determination of $T_{eff}$ is explained in a separate section here below.

In the case of effluent dose:

$$Deff\_computed = D\_need \times \frac{T\_prosp}{T\_eff}$$

This means that an effluent flow rate change ($\Delta Q_{eff} = D_{eff\_computed} - Q_{eff\_current}$) has to be imposed and this of course impacts on the new set flow rate for the effluent line, which has to be balanced by one or more of PBP, Dialysate and Replacement flow rates. Different rules can be applied to balance the new flow rate in the effluent line.

In one aspect, the change $\Delta Q_{eff}$ can be balanced over Dialysate and Replacement flow rates only In an alternative aspect, the change $\Delta Q_{eff}$ can be balanced over all 3 flow rates: namely, PBP, Dialysate and Replacement flow rates.

In a further alternative aspect, the change $\Delta Q_{eff}$ can be balanced over one of PBP, Dialysate and Replacement flow rates.

Moreover, the splitting of $\Delta Q_{eff}$ can be done according to different rules; for instance: $\Delta Q_{eff}/N$ change could be equally split on each of the N selected flows. Alternatively $\Delta Q_{eff}$ could be split by keeping the current Dial/Rep ratio:

$\Delta Q_{dial} = \Delta Q_{eff} \times Q_{dial}/(Q_{dial}+Q_{rep})$ $\Delta Q_{rep} = \Delta Q_{eff} \times Q_{rep}/(Q_{dial}+Q_{rep})$ Down Time Estimates Estimating 'future' down times is the process needed to get $T_{eff}$. The control unit is configured to execute such process. Several types of down-times can be estimated:
Related to bag management: this is dependent on the flow rates and volumes of bag in use for the number of bag changes to be expected over $T_{prosp}$+mean time estimate for changing a bag. Statistical values can be built-in the system and derived from a large panel of field records and/or computed over the current treatment or the current patient or over machine history (in the medical unit) in order to consider the specific circumstances.
Related to alarms other than bag changes: also this can be derived from a statistical analysis.
Related to change of set:
Change of set can be considered if reach maximum set life (e.g.: 72 h) during the $T_{prosp}$ period
Advanced system might anticipate a change of set on the basis of pressure profiles and/or statistics of set life on current patient.
A mean time estimate for changing a set can be used which can be derived from statistical analysis

EXAMPLE 2: FLOW CORRECTION AND TEFF ESTIMATION

CVVHDF treatment initially prescribed with:
dialysate flow $Q_{dial0}$=2000 ml/h
replacement flow $Q_{rep0}$=1000 ml/h
patient fluid removal $Q_{prf0}$=100 ml/h
Effluent flow is $Q_{eff0}=Q_{dial0}+Q_{rep0}+Q_{prf0}$=3100 ml/h
Dose prescription is: Dose$_{eff}$=3100 ml/h
Volume of dialysate and replacement solution containers (e.g. solution bags) are $V_{dial}=V_{rep}$=5000 ml
Effluent is collected in bags of volume $V_{eff}$=8000 ml
At the time $T_0$ of $T_{eff}$ estimation, the set has been already in use for 65 hours and has to be changed after 72 hours. Treatment interruption time related to a change of set ($T_{change\_set}$) is estimated statistically as 66 min=1.10 hour.
$T_{prosp}$=24 hours.

Dose Need

Over the time period $T_{retro}$=24 hours a total effluent volume of 72 000 ml has been collected, meaning a delivered dose D_del=72000/24=3000 ml/h
Dose$_{need}$ over $T_{prosp}$ is then:

$$Dose\_need = \frac{3100 \times 24 + (3100 - 3000) \times 24}{24} = 3100 + 100 = 3200 \text{ ml/h}$$

Down Times and T_eff

In this example, the constant correction coefficient K is representative of the $2^{nd}$ item (alarms) of the list presented in the section "down times".

Time spent in therapy/run mode over time window Tprosp: Trun=Tprosp−Tchange_set
Treatment time lost because of alarms: Tdown$_{alarms}$=K$_{alarms}$×Trun, where K$_{alarms}$=0.01 has a statistical definition.
Treatment time lost because of bag changes: Tdown$_{bags}$=Tdown$_{bag\_eff}$+Tdown$_{bag\_dal}$+Tdown$_{bag\_rep}$
Number of bag change for Dialysate:

$$N_{bag\_dial} = \frac{Qdial}{Vdial} \times (Trun - Tdown_{alarms} - Tdown_{bags})$$

Similar formula for number of bag changes on Replacement and Effluent lines.
The time required for changing a bag (from statistical analysis) can be: Tchange_bag=2 min
Final expression of down time related to bags:

$$Tdown_{bags} = Tdown_{bag\_eff} + Tdown_{bag\_dal} + Tdown_{bag\_rep}$$

$$Tdown_{nags} =$$

$$\frac{alpha}{1+alpha} \times (Trun - Tdown_{alarms}) = \frac{alpha}{1+alpha} \times (1 - K_{alarms}) \times Trun$$

$$\text{With alpha} = \left(\frac{Qeff}{Veff} + \frac{Qdial}{Vdial} + \frac{Qrep}{Vrep}\right) \times T_{change\_bag}$$

Effective run time during time window Tprosp:
$T$eff=$T$run−Tdown$_{alarms}$−Tdown$_{bags}$ (Instantaneous) effluent flow to be set to achieve the delivery of Dose_need over Tprosp time:

$$Qeff1 = Dose\_need \times \frac{T\_prosp}{T\_eff} = 3200 \times \frac{24}{T\_eff}$$

The last equation (for Qeff1) includes the term T_eff, which is a function of effluent flow rate and other flows. A numerical iterative method will easily solve the set of equations and provide for the Qeff1 value. Before achieving this, the rule for changing Dial and Rep flow in correlation to the required Eff flow change is to be chosen.

Below results for the given example are computed with the rule:

$$Qdial1 = Qdial0 + \frac{Qdial0}{Qdial0 + Qrep0} \times (Qeff1 - Qeff0)$$

$$Qrep1 = Qrep0 + \frac{Qrep0}{Qdial0 + Qrep0} \times (Qeff1 - Qeff0)$$

Solutions to the example:
Qeff1=3514 ml/h,
Qdial=2276 ml/h,
Qrep=1138 ml/h,
Tdown$_{bags}$=0.82 h.

Thus, more in general, the effective portion of the remaining treatment time can be calculated as a function of a number of K factors, which can at least in part be statistically determined, as explained in the section "down times". Once the effective treatment time is determined, the control unit is configured to calculate, at a certain instant t during treatment, said updated flows based on: the dose need, which depends upon the delivered dose and the prescribed dose, the effective treatment time portion $T_{eff}$.

Then the control unit will control the means for regulating the flow rate, e.g. pumps 21 and 18 in the example of FIG. 1 with the above new set values for the next time interval until the next check point (step 50). The control unit is also configured to automatically repeat the above described flow rate update procedure. For instance, the flow rate update procedure is periodically repeated after time periods of no less than two hours, preferably every 4 or 6 hours (see step 51).

EXAMPLE 3—CASE OF CHANGE OF DOSE PRESCRIPTION D_SET

The control unit can also be configured to run a flow update procedure in case there is a change in the Dose prescription. In practice, the control unit detects the change in prescription and runs the flow update procedure thereafter.

First Flow Update

In an aspect, an update of flow parameters is performed immediately after a change of dose prescription.

Parameters of previous example 2 are revisited in the case where the flow update is triggered by a change of prescribed dose.

Unchanged parameters (settings before T0):
CVVHDF treatment initially prescribed with:
dialysate flow Q$_{dial0}$=2000 ml/h
replacement flow Q$_{rep0}$=1000 ml/h
patient fluid removal Q$_{pfr0}$=100 ml/h
Effluent flow is Q$_{eff0}$=Q$_{dial0}$+Q$_{rep0}$+Q$_{pfr0}$=3100 ml/h
Dose prescription is: Dose$_{eff0}$=3100 ml/h
Volume of dialysate and replacement solution containers (e.g. solution bags) are V$_{dial}$=V$_{rep}$=5000 ml.
Effluent is collected in bags of volume V$_{eff}$=8000 ml.
At the time T$_0$, the set has been already in use for 65 hours and has to be changed after 72 hours. Treatment interruption time related to a change of set (T$_{change\_set}$) is estimated statistically as 66 min=1.10 hour.
T$_{prosp}$=24 hours.
At the time T$_0$, dose prescription is moved to:
Dose$_{eff1}$=3500 ml/h.

Dose Need

Over the time period T$_{retro}$=24 hours a total effluent volume of 72 000 ml has been collected, meaning a delivered dose D$_{del}$=72000/24=3000 ml/h
Dose needed over T$_{prosp}$ is then:

$$\text{Dose\_need} = \frac{3500 \times 24 + (3100 - 3000) \times 24}{24} = 3500 + 100 = 3600 \text{ ml/h}$$

Down Times and T_eff

Equations are exactly the same as in previous example.
With the new value of Dose$_{need}$, flow rates solutions become:
Q$_{eff1}$=3973 ml/h, Q$_{dial}$=2582 ml/h, Q$_{rep}$=1291 ml/h
Tdown$_{bags}$=0.92 h
Note: flow computation keeping the planned change set at 72 h as in previous example 2

Next Flow Updates

For the next periodic flow updates (period ΔT), the computation of dose gap over time period Tretro needs to consider the change of prescription.

Dose gap has to be computed over each time period with constant dose.

Continuation of previous example with following additional data:
(T$_0$: time of dose prescription change)
ΔT=4 hours; T$_1$=T$_0$+ΔT
Volume delivered over time period [T$_1$-24; T$_0$] (20 hours): 60500 ml/set dose Dose_eff0
Volume delivered over time period [T$_0$; T$_1$] (4 hours): 14700 ml/set dose Dose$_{eff1}$ Dose_need =

$$\frac{3500 \times 24 + [(3100 - 60500/20) \times 20 + (3500 - 14700/4) \times 4]}{24} \text{ ml/h}$$

Dose_need =

$$3500 + \frac{[(3100 - 3025) \times 20 + (3500 - 3675) \times 4]}{24} = 3500 + 33 = 3533 \text{ ml/h}$$

Flow rate solutions are:
Q$_{eff1}$=3895 ml/h, Q$_{dial}$=2530 ml/h, Q$_{rep}$=1265 ml/h
Tdown$_{bags}$=0.90 h
Note: flow computation keeping the planned change set at 72 h as in previous example 2 (T1=T0+4 h=69 h<72 h)

Although the above examples focused on the case of the dose being the effluent fluid dose D$_{eff}$, the control unit is configured to give the operator several dose options, as already mentioned, namely:
effluent dose D$_{eff}$: the flow rate Q$_{eff}$,
convective dose D$_{conv}$: the sum of the flow rates Q$_{rep}$+Q$_{pbp}$+Q$_{pfr}$, where Q$_{pfr}$ represents the patient fluid removal rate, diffusive dose $D_{dial}$: the flow rate $Q_{dial}$,
urea dose $D_{urea}$: estimated urea clearance,
clearance dose: an estimated clearance for a given solute.

In general the flow rates update procedure takes into account for the dose option and for the selected treatment.

EXAMPLE 4—FIG. 4

Figure 4:
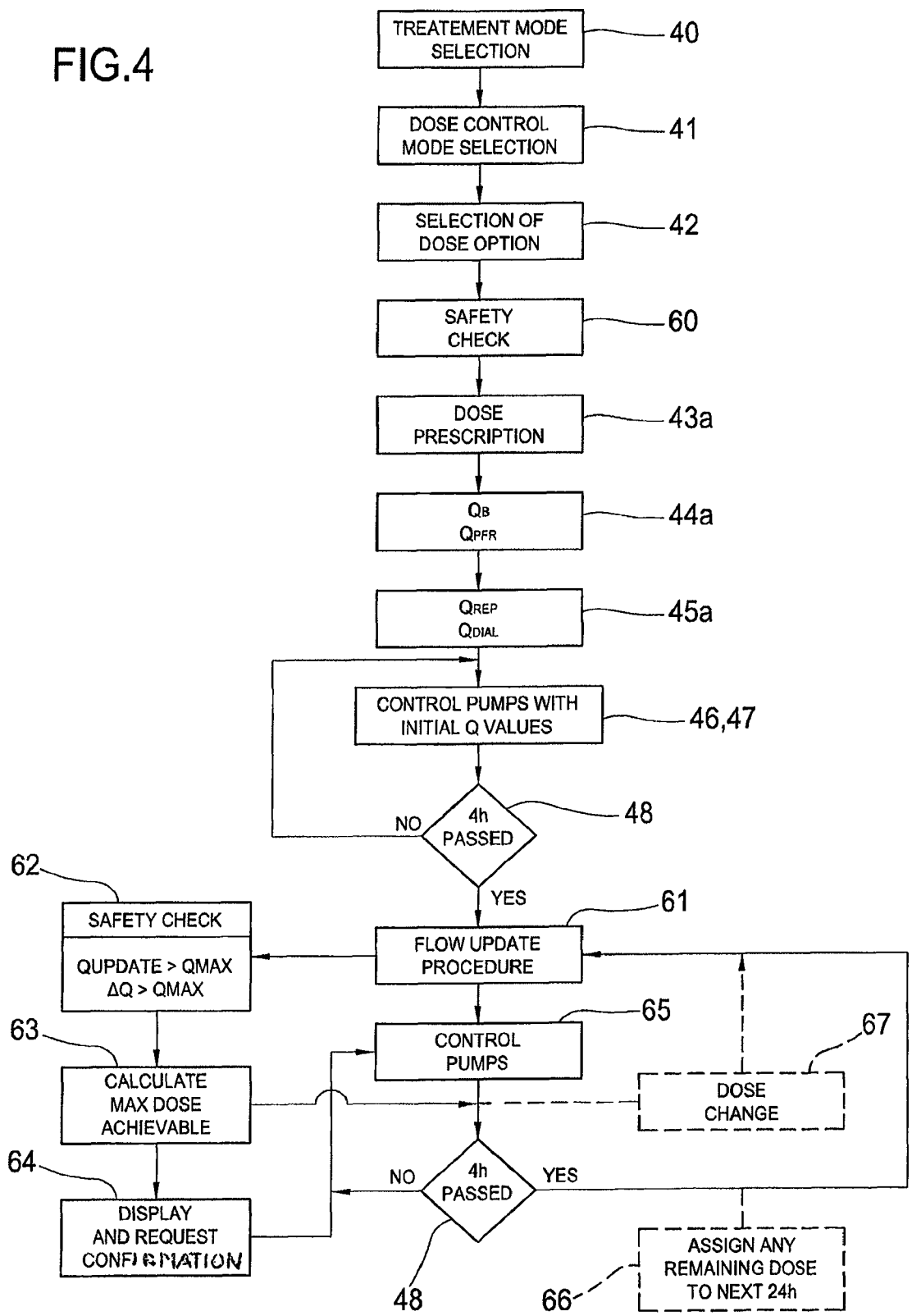
FIG. 4 shows a block diagram of another update procedure executable by a control unit according to a further aspect of the invention.

FIG. 4, schematically shows further aspects of the invention and relates to an alternative sequence of steps the control unit 1 may be configured to execute. Steps common to those described in connection with FIG. 3 are referenced with same numerals and are not described again.

After steps 41, 42 and 43, once the user has selected the treatment mode and decided to enter in dose control mode, the control unit may be programmed to check (step 60 in FIG. 4) whether the selected treatment mode and the dose control mode are conflicting modes and prevent from entering in dose control mode in case of conflict between the selected treatment mode and the dose control mode. For instance, in case a treatment mode is selected where use is made of said pre-blood pump infusion line for regional anticoagulation using e.g. citrate then entering in dose control mode is prevented.

Then the control unit is configured to receive a set prescription for the hourly dose of e.g. the effluent fluid (step 43a) and set values for the blood flow $Q_B$ and patient fluid removal rate $Q_{PFR}$ rate (step 44a) and to receive or calculate initial set values for the dialysis and replacement fluid flow rates (45a). At step 46 and 47, the above rates are set as initial values and implemented by the control unit controlling the respective pumps. Periodically (see steps 48) a flow rate update procedure (step 61), e.g. comprising steps as described in above section "flow rate update procedure" is executed. Moreover, each time new updated values of the flow rates are calculated as above described, the control unit will run a safety check to make sure that the new flow rates are compatible with certain safety criteria (step 62): for instance each set flow rate cannot pass a respective maximum threshold value; moreover, the variation between the values of each updated flow rate and the respective previous flow rate (which can be one of the initial flow rates or a previously updated flow rate value) should preferably not be excessive and is also controlled to be below a respective threshold.

Furthermore, the control unit 10 can be configured to also calculate a maximum achievable dose (step 63) within said safety criteria, and to assess whether said prescribed dose can be reached. In the affirmative, the control unit can be configured to control the means for regulating the flow rates such as to achieve the prescribed dose within the prescribed time interval. Alternatively, the control unit could be configured to control the means for regulating the flow rates to achieve the maximum dose possible within said prescribed time interval in a manner compatible with the safety criteria.

If, instead, it is determined that the prescribed dose is higher than the maximum achievable dose, then the control unit is programmed to calculate a remaining dose as a difference between the prescribed dose and the maximum dose actually achievable within the prescribed time interval. As mentioned, the control unit is designed to control the apparatus in term of flow rates, thus after a number of check points it may be possible to recover the any remaining dose accumulated in previous time intervals (step 66).

As a further safety measure, or in alternative to the safety criteria above described, the control unit may be programmed to display on the user interface 12 the calculated updated set of values for said flow rates, and to prompt user to confirm the updated set of values (step 64) for said flow rates before using the updated values for controlling the means for regulating (step 65). If the user approves the updated set of values, then the control unit 10 is programmed to use the updated flow rate values as new set values for controlling the means for regulating the fluid flow through the fluid flow lines. In practice, referring to the example of FIG. 1, once the updated values for the effluent flow rate, infusion flow rate and dialysis liquid flow rate are determined, these values are used to control the speed of the respective pumps, namely the effluent pump, the dialysis fluid pump and the infusion pump. Note that the step of displaying the updated values and asking for user's approval (step 64) is optional.

The step of calculating updated values of the flow rates is affected by the selected dose option and by the type of apparatus and treatment mode selected. For instance if the effluent dose is the dose option and if the treatment mode is a pure HF (i.e. there is no dialysis liquid container), then the flow rate update procedure will not generate an updated dialysis fluid flow rate. In one embodiment, where both the infusion line and the dialysis line are used (HDF configuration), the step of calculating the updated set of values comprises calculating an updated infusion pump flow rate and an updated dialysis pump flow rate, as above described with reference to FIG. 1. Preferably, the updated infusion pump flow rate and the updated dialysis fluid flow rate differ from their respective initial values by a same percentage. Alternatively, the step of calculating the updated set of values may comprise calculating an updated infusion pump flow rate without changing the dialysis pump flow rate: in other words if the effluent volume dose is the dose to be achieved the control unit may be configured to achieve said dose without varying the dialysis fluid flow rate and only acting on the effluent pump and on the infusion pump. Analogously, the control unit may be programmed to only update the dialysis fluid flow rate and not the infusion fluid flow rate: this is typically the case when the infusion line is a pre-dilution line, i.e. an infusion line connected upstream the filtration unit in a so called "pre dilution" configuration.

In a configuration where the apparatus comprises both a pre-dilution and a post-dilution line the control unit can be configured for calculating an updated infusion pump flow rate by calculating an updated pre-dilution pump flow rate and an updated post-dilution pump flow rate: the updated pre-dilution pump flow rate and the updated post-dilution pump fluid flow rate may differ from their respective initial values by a same percentage.

It should be noted that the control unit is configured during the flow update procedure to leave the set blood pump flow rate unchanged to its initial set value.

In accordance with a further aspect, which may be additional or alternative to one or more of the above disclosed aspects, the control unit 10 is programmed to allow a user to vary the initial value for the dose of the substance. In this case, the control unit is programmed to receive the new dose value (step 67) and to calculate corresponding updated values for the flow rates through the fluid flow lines in order to arrive as close as possible and possibly match said new dose value.

For instance, a first value for the prescribed dose ($D_0$) can be entered before treatment start ($T_0$); then after a while (instant $T_t$) from treatment start, a second different value of the prescribed dose ($D_1$) to be reached can be entered. In this case, the control unit, after receipt of said second value, is configured to calculate the updated set of values based upon:

said second value for the dose ($D_1$),
the time at which said second value is entered ($T_1$),
predetermined reference time interval (T) across which the second value for the dose has to be delivered.

In making the calculation, the control unit can also be programmed to account for the fraction of dose $D_t$ already delivered at time $T_t$ and for the effective remaining treatment time $K*(T-T_t)$.

Going into the description of further aspects of the apparatus of FIGS. 1 and 2, the apparatus 1 also comprises a first scale 32 operative for providing weight information relative to the amount of the fluid collected in the effluent fluid container 14; a second scale 33 operative for providing weight information relative to the amount of the fluid supplied from the infusion fluid container 16; a third scale 34 operative for providing weight information relative to the amount of the fluid supplied from dialysis fluid container 20. In case more infusion lines would be present, as infusion lines 21 and 25 in FIG. 2, then a respective fourth and fifth scale 36 and 37 could be present to provide weight information relative to the amount of fluid supplied from infusion container 23 and from infusion container 26. The scales are all connected to the control unit and provide said weight information for the control unit to determine the actual quantity of fluid in each container as well as the actual flow rate of fluid supplied by or received in each container. The control unit 10 may then be configured to receive treatment selection information and check if the user entered into dose control mode. The control unit can also be configured to receive weight information from the first scale and, depending upon the selected treatment, from the scales associated to the container supplying the lines involved in the delivery of the selected treatment) and to control, at least at the beginning of the treatment, the flow rate of at least one of the effluent fluid, the infusion fluid, the dialysis fluid by controlling said means for regulating based on said weight information, and said initial set values. Then, at time intervals after start of the treatment, the control unit is configured to execute the flow update procedure as above described calculating said updated set of values, and subsequent to each said calculation, controlling the flow rate of at least one of the effluent fluid, the infusion fluid, the dialysis fluid by controlling said means for regulating based on said weight information, and said updated set of values.

From a structural point of view one or more, optionally all containers 14, 16, 20, 23 may be disposable plastic containers, preferably bags which are hang on a support carried by the respective scale. All lines and the filtration unit may also be plastic disposable components which can be mounted at the beginning of the treatment session and then disposed of at the end of the treatment session. The means for regulating typically may comprise pumps, although other regulating means as valves or combinations of valves and pumps could be used. The scales may comprise piezoelectric sensors, or strain gauges, or spring sensors, or any other type of transducer able to sense forces applied thereon. Although the examples in the figures show use of scales for determining the amount of fluid in the respective containers and for allowing calculation of the respective flow rates through the various lines, it should be noted that the above described aspects of the invention are compatible also with blood treatment machines using volumetric sensors for determining flow rates or combinations of mass and volumetric sensors.

The invention claimed is:

1. An apparatus for extracorporeal treatment of blood comprising:
  a filtration unit having a primary chamber and a secondary chamber separated by a semi-permeable membrane;
  a blood withdrawal line connected to an inlet of the primary chamber;
  a blood return line connected to an outlet of the primary chamber, said blood withdrawal line and said blood return line being configured to be connected to a cardiovascular system of a patient;
  a blood pump configured for controlling a flow of the blood through the blood withdrawal line;
  an effluent fluid line connected to an outlet of the secondary chamber;
  at least two fluid lines comprising:
    a pre-blood pump infusion line connected to the blood withdrawal line in a region of the blood withdrawal line that is positioned upstream of the blood pump, and
    at least one of (i) a pre-dilution fluid line connected to the blood withdrawal line, (ii) a post-dilution fluid line connected to the blood return line, and (iii) a dialysis fluid line connected to an inlet of the secondary chamber;
  at least two pumps selected from (i) a pre-blood pump configured to pump through the pre-blood pump infusion line, (ii) a pre-dilution pump configured to pump through the pre-dilution fluid line, (iii) a post-dilution pump configured to pump through the post-dilution fluid line, and (iv) a dialysis fluid pump configured to pump through the dialysis fluid line connected to the inlet of the secondary chamber; and
  a control unit configured to:
    calculate or receive initial set values of two or more fluid flow rates selected from the group including a fluid flow rate ($Q_{eff}$) through the effluent fluid line, a fluid flow rate ($Q_{rep}$) through the pre-dilution fluid line or the post-dilution fluid line, a fluid flow rate ($Q_{pbp}$) through the pre-blood pump infusion line, a fluid flow rate ($Q_{dial}$) through the dialysis fluid line, and a fluid removal rate ($Q_{pfr}$) from the patient,
    receive at least a prescribed dose ($D_{set}$) or calculate said prescribed dose ($D_{set}$) as a target mean value of one or more flow rates to be delivered across an entire patient treatment,
    execute a flow rate update procedure comprising calculating updated set values for one or more of said fluid flow rates based on said prescribed dose ($D_{set}$) in order to deliver the prescribed dose ($D_{set}$) via the pre-blood pump and/or at least one of (i) the pre-dilution pump, (ii) the post-dilution pump, and (iii) the dialysis fluid pump during a reference time interval, wherein the initial set value of the fluid flow rate ($Q_{pbp}$) through the pre-blood pump infusion line is maintained at the initial set value of the fluid flow rate ($Q_{pbp}$) when the updated set values are calculated, and
    cause the at least two pumps to operate at the one or more of said fluid flow rates based on the updated set values based on said prescribed dose ($D_{set}$) in order to deliver the prescribed dose ($D_{set}$) via the pre-blood pump and/or at least one of (i) the pre-dilution pump, (ii) the post-dilution pump, and (iii) the dialysis fluid pump.

2. The apparatus for extracorporeal treatment of blood according to claim 1, wherein the step of calculating the updated set values comprises maintaining the initial set value of the fluid removal rate ($Q_{pfr}$) from the patient at the initial set value of the fluid removal rate ($Q_{pfr}$).

3. The apparatus for extracorporeal treatment of blood according to claim 1, wherein the control unit is configured to receive an initial set value for a blood pump flow rate and to control said blood pump accordingly, and wherein the step of calculating said updated set values comprises maintaining the initial set value of the blood pump flow rate at the initial set value of the blood pump flow rate.

4. The apparatus for extracorporeal treatment of blood according to claim 1, wherein said prescribed dose ($D_{set}$) comprises a prescribed value for one flow rate selected in the group including:
an effluent dose flow rate ($D_{eff\_set}$), which is a prescribed mean value of the fluid flow rate ($Q_{eff}$) through the effluent fluid line,
a convective dose flow rate ($D_{conv\_set}$), which is a prescribed mean value of a sum of the fluid flow rate ($Q_{rep}$) through the pre-dilution fluid line and the fluid flow rate ($Q_{rep}$) through the post-dilution fluid line, the fluid flow rate ($Q_{pbp}$) through the pre-blood pump infusion line, and the fluid removal rate ($Q_{pfr}$) from the patient,
a diffusive dose flow rate ($D_{dial\_set}$), which is a prescribed mean value of the fluid flow rate ($Q_{dial}$) through the dialysis fluid line,
a urea dose ($D_{urea\_set}$), which is a prescribed mean value for an estimated urea clearance, and
a clearance dose ($K_{solute\_set}$), which is a prescribed mean value for an estimated clearance for a given solute.

5. The apparatus for extracorporeal treatment of blood according to claim 1, wherein the control unit is configured to regularly execute said flow rate update procedure at check points during the patient treatment, and wherein the flow rate update procedure comprises the following steps:
determining a value of a dose delivered ($D_{del}$) over a time interval ($T_{retro}$) preceding a respective check point ($T_i$),
determining a dose need value ($D_{need}$) at the respective check point ($T_i$) based at least on the value of the dose delivered ($D_{del}$) and on the prescribed dose ($D_{set}$), and
calculating the updated set values for the one or more of said fluid flow rates based on the dose need value ($D_{need}$).

6. The apparatus for extracorporeal treatment of blood according to claim 5, wherein determining the dose need value ($D_{need}$) at the respective check point ($T_i$) comprises computing a dose needed to be delivered over a next time period ($T_{prosp}$) following the respective check point ($T_i$) in order to reach the prescribed dose ($D_{set}$) over the reference time interval, wherein the reference time interval is a sum of (i) the time interval ($T_{retro}$) preceding the respective check point ($T_i$) and (ii) the next time period ($T_{prosp}$), and wherein the dose need value ($D_{need}$) is calculated at the respective check point ($T_i$) according to the formula:

$$D_{need} = \frac{(D_{set})(T_{prosp}) + (D_{set} - D_{del})(T_{retro})}{T_{prosp}}$$

wherein:
$D_{del}$ is the dose delivered over the time interval ($T_{retro}$) preceding the respective check point ($T_i$),
$D_{need}$ is the dose need value,
$T_{retro}$ is the time interval preceding the respective check point ($T_i$),
$T_{prosp}$ is the next time period following the respective check point ($T_i$), and
$D_{set}$ is the prescribed dose over the reference time interval.

7. The apparatus for extracorporeal treatment of blood according to claim 6, wherein the control unit is programmed to determine an effective portion ($T_{eff}$) of the next time period ($T_{prosp}$), and wherein a corrected dose value ($D_{computed}$) is calculated as follows:

$$D_{computed} = D_{need} \frac{T_{prosp}}{T_{eff}}$$

wherein the flow rate update procedure includes calculating the updated set values for the one or more fluid flow rates based on the corrected dose value ($D_{computed}$) to account for the effective portion of the next time period.

8. An apparatus for extracorporeal treatment of blood comprising:
a filtration unit having a primary chamber and a secondary chamber separated by a semi-permeable membrane;
a blood withdrawal line connected to an inlet of the primary chamber;
a blood return line connected to an outlet of the primary chamber, said blood withdrawal line and said blood return line being configured to be connected to a cardiovascular system of a patient;
a blood pump configured for controlling a flow of the blood through the blood withdrawal line;
an effluent fluid line connected to an outlet of the secondary chamber;
at least two fluid lines comprising:
a pre-blood pump infusion line connected to the blood withdrawal line in a region of the blood withdrawal line that is positioned upstream of the blood pump, and
at least one of (i) a pre-dilution fluid line connected to the blood withdrawal line, (ii) a post-dilution fluid line connected to the blood return line, and (iii) a dialysis fluid line connected to an inlet of the secondary chamber;
at least two pumps selected from (i) a pre-blood pump configured to pump through the pre-blood pump infusion line, (ii) a pre-dilution pump configured to pump through the pre-dilution fluid line, (iii) a post-dilution pump configured to pump through the post-dilution fluid line, and (iv) a dialysis fluid pump configured to pump through the dialysis fluid line connected to the inlet of the secondary chamber;
a user interface; and
a control unit connected to the user interface and configured to:
calculate or receive set values of two or more fluid flow rates selected from the group including: a fluid flow rate ($Q_{eff}$) through the effluent fluid line, a fluid flow rate ($Q_{rep}$) through the pre-dilution fluid line or the post-dilution fluid line, a fluid flow rate ($Q_{pbp}$) through the pre-blood pump infusion line, a fluid flow rate ($Q_{dial}$) through the dialysis fluid line, and a fluid removal rate ($Q_{pfr}$) from the patient,
display on the user interface an indicium prompting a user to select whether to enter a dose control mode,
responsive to detecting that the user selected to enter the dose control mode:
calculate a prescribed dose ($D_{set}$) based on initial set values of the two or more fluid flow rates or display an indicium prompting a user to enter the prescribed dose ($D_{set}$), wherein the prescribed dose is a target mean value of one or more flow rates to be delivered across an entire patient treatment, execute a flow rate update procedure comprising calculating updated set values of the one or more fluid flow rates based on the prescribed dose ($D_{set}$) in order to deliver the prescribed dose ($D_{set}$) via the pre-blood pump and/or at least one of (i) the pre-dilution pump, (ii) the post-dilution pump, and (iii) the dialysis fluid pump during a reference time interval, wherein the initial set value of the fluid flow rate ($Q_{pbp}$) through the pre-blood pump infusion line is maintained at the initial set value of the fluid flow rate ($Q_{pbp}$) when the updated set values are calculated, and control said at least two pumps to operate at the one or more of said fluid flow rates based on the updated set values based on said prescribed dose ($D_{set}$) in order to deliver the prescribed dose ($D_{set}$) via the pre-blood pump and/or at least one of (i) the pre-dilution pump, (ii) the post-dilution pump, and (iii) the dialysis fluid pump, and responsive to detecting that the user selected to not enter the dose control mode:
display on the user interface an indicium prompting a user to enter, via the user interface, set values of two or more of said fluid flow rates, and
control said at least two pumps to operate based on said set values entered via the user interface.

9. The apparatus for extracorporeal treatment of blood according to claim 8, wherein the prescribed dose ($D_{set}$) comprises a prescribed value for one flow rate selected from the group including:
an effluent dose flow rate ($D_{eff\_set}$), which is a prescribed mean value of the fluid flow rate ($Q_{eff}$) through the effluent line, the flow rate through the effluent fluid line,
a convective dose flow rate ($D_{conv\_set}$), which is a prescribed mean value of a sum of the fluid flow rate ($Q_{rep}$) through the pre-dilution fluid line and the fluid flow rate ($Q_{rep}$) through the post-dilution fluid line, the fluid flow rate ($Q_{pbp}$) through the pre-blood pump infusion line, and the fluid removal rate ($Q_{pfr}$) from the patient,
a diffusive dose flow rate ($D_{dial\_set}$), which is a prescribed mean value of the fluid flow rate ($Q_{dial}$) through the dialysis fluid line,
a urea dose ($D_{urea\_set}$), which is a prescribed mean value for an estimated urea clearance, and
a clearance dose ($K_{solute\_set}$), which is a prescribed mean value for an estimated clearance for a given solute.

10. The apparatus for extracorporeal treatment of blood according to claim 8, wherein responsive to detecting that the user selected to enter the dose control mode, the control unit is configured to regularly execute the flow rate update procedure at check points during the patient treatment, and wherein the flow rate update procedure comprises the following steps:
determining a value of a dose delivered ($D_{del}$) over a time interval ($T_{retro}$) preceding a respective check point ($T_i$), determining a dose need value ($D_{need}$) at the respective check point ($T_i$) based at least on the value of the dose delivered ($D_{del}$) and on the prescribed dose value ($D_{set}$), and
calculating the updated set values for the two or more fluid flow rates based on the dose need value ($D_{need}$).

11. The apparatus for extracorporeal treatment of blood according to claim 10, wherein determining the dose need value ($D_{need}$) at the respective check point ($T_i$) comprises computing a dose needed to be delivered over a next time period ($T_{prosp}$) following the respective check point ($T_i$) in order to reach the prescribed dose over the reference time interval, wherein the reference time interval is a sum of (i) the time interval ($T_{retro}$) preceding check point ($T_i$) and (ii) the next time period ($T_{prosp}$), and wherein the dose need value ($D_{need}$) is calculated at the respective check point ($T_i$) according to the formula:

$$D_{need} = \frac{(D_{set})(T_{prosp}) + (D_{set} - D_{del})(T_{retro})}{T_{prosp}}$$

where:
$D_{del}$ is the dose delivered over the time interval ($T_{retro}$) preceding the respective check point ($T_i$),
$D_{need}$ is the dose need value,
$T_{retro}$ is the time interval preceding the respective check point ($T_i$),
$T_{prosp}$ is the next time period following the respective check point ($T_i$), and
$D_{set}$ is the prescribed dose value over the reference time interval.

12. The apparatus for extracorporeal treatment of blood according to claim 11, wherein the control unit is programmed to determine an effective portion ($T_{eff}$) of the next time period, and wherein a corrected dose value ($D_{computed}$) is calculated as follows:

$$D_{computed} = D_{need} \frac{T_{prosp}}{T_{eff}}$$

wherein the flow rate update procedure includes calculating the updated set values for the one or more fluid flow rates based on the corrected dose value ($D_{computed}$) to account for the effective portion of the next time period.

13. The apparatus for extracorporeal treatment of blood according to claim 8, wherein the flow rate update procedure comprises:
displaying on the user interface the updated set values that are calculated for the one or more flow rates,
prompting the user to confirm the updated set values for the one or more flow rates, and
responsive to the user approving the updated set values for the one or more flow rates, controlling the at least two pumps to operate based on the updated set of values for the one or more flow rates.

* * * * *